US010538805B2

(12) United States Patent
Spizz et al.

(10) Patent No.: US 10,538,805 B2
(45) Date of Patent: Jan. 21, 2020

(54) QUANTITATIVE MULTIPLEXED IDENTIFICATION OF NUCLEIC ACID TARGETS

(71) Applicant: Rheonix, Inc., Ithaca, NY (US)

(72) Inventors: Gwendolyn Spizz, Ithaca, NY (US); Peng Zhou, Newtown, PA (US)

(73) Assignee: Rheonix, Inc., Ithica, NY (US)

( * ) Notice: Subject to any disclaimer, the term of this patent is extended or adjusted under 35 U.S.C. 154(b) by 675 days.

(21) Appl. No.: 14/983,913

(22) Filed: Dec. 30, 2015

(65) Prior Publication Data

US 2016/0138099 A1 May 19, 2016

Related U.S. Application Data

(62) Division of application No. 13/273,522, filed on Oct. 14, 2011, now Pat. No. 9,284,613.
(60) Provisional application No. 61/393,253, filed on Oct. 14, 2010.

(51) Int. Cl.
*C12Q 1/68* (2018.01)
*C12Q 1/6851* (2018.01)
*C12Q 1/689* (2018.01)
*C12Q 1/70* (2006.01)
*C12Q 1/6806* (2018.01)

(52) U.S. Cl.
CPC ......... *C12Q 1/6851* (2013.01); *C12Q 1/6806* (2013.01); *C12Q 1/689* (2013.01); *C12Q 1/707* (2013.01); *C12Q 1/708* (2013.01)

(58) Field of Classification Search
None
See application file for complete search history.

(56) References Cited

U.S. PATENT DOCUMENTS

| | | |
|---|---|---|
| 5,789,153 A | 8/1998 | Falkner |
| 6,613,520 B2 | 9/2003 | Ashby |
| 6,656,687 B1 | 12/2003 | Hyldig-Nielsen |
| 6,794,167 B2 | 9/2004 | Parales |
| 6,849,430 B2 | 2/2005 | Carson |
| 7,118,867 B2 | 10/2006 | Tabiti |
| 7,405,044 B2 | 7/2008 | Walker |
| 7,759,057 B2 | 7/2010 | Zhou |
| 8,012,691 B2 | 9/2011 | Shewale |
| 2002/0150887 A1 | 10/2002 | Maruyama |
| 2003/0087397 A1 | 5/2003 | Klein |
| 2004/0161767 A1 | 8/2004 | Baldwin |
| 2008/0261206 A1 | 10/2008 | Kim |
| 2009/0227476 A1 | 9/2009 | Malcolm |
| 2009/0275025 A1 | 11/2009 | Rihet |
| 2010/0323910 A1 | 12/2010 | Wunch |
| 2011/0136104 A1 | 6/2011 | Pregibon |

FOREIGN PATENT DOCUMENTS

| | | |
|---|---|---|
| JP | 2000316560 | 11/2000 |
| WO | 2006104381 | 10/2006 |

OTHER PUBLICATIONS

Innings, et al. (J Clin Microbiol, 2007, 45(3):874-880) (Year: 2007).*
Hamels et al. (Biotechniques, 2001, 31(6):1364-1372) (Year: 2001).*
Eichmann, et al. (Int J Legal Med, 2008, 122:385-388) (Year: 2008).*
Niederstatter et al. (Forensic Sci Intl:Genetics, 2007, 29-34) (Year: 2007).*
Smith et al. (J of Lipid Research, 2004, vol. 45, p. 686-696) (Year: 2004).*
Dieter Klein, Quantification using real-time PCR technology: applications and limitations, Trends in Molecular Medicine, vol. 8 No. 6, Jun. 2002, 257-260.
Thompson et al.; Clustal W: improving the sensitivity of progressive multiple sequence alignment through sequence weighting, position-specific gap penalties and weight matrix choice, Nucleic Acids Research, 1994, vol. 22, No. 22, 4673-4680, 1994 Oxford University Press.
Weller et al., Detection of Ralstonia solanacearum Strains with a Quantitative, Multiplex, Real-Time, Fluorogenic PCR (TaqMan) Assay; Applied and Environmental Microbiology, Jul. 2000, 2853-2858, American Society for Microbiology.
Supplemental European Search Report, European Patent Office; Munich; EP Application No. 11 83 3469, dated Mar. 28, 2014, pp. 1-9.
Yang, Samuel et al; Quantitative Multiprobe PCR Assay for Simultaneous Detection and Identification to Species Level of Bacterial Pathogens; Journal of Clinical Microbiology; vol. 40, No. 9; Sep. 2002; 3449-3454; American Society for Microbiology.
Ott, Stephan J. et al.; Quantification of Intestinal Bacterial Populations by Real-Time PCR with a Universal Primer Set and Minor Groove Binder Probes: a Global Approach to the Enteric Flora; Journal of Clinical Microbiology, Jun. 2004; 2566-2572; American Society for Microbiology.
Maity, B et al; Development of a Macroarray Based on 16S-23S rDNA Probe Hybridization for Rapid Diagnosis of Human Pathogenic Bacteria; Indian Journal of Biotechnology; vol. 7; Oct. 2008; 448-455.
Rougemont, M. et al., Dec. 2004, "Detection of Four *Plasmodium* Species in Blood from Humans by 18S rRNA Gene Subunit-Based and Species-Specific Real-Time PCR Assays", Journal Clinical Microbiology, vol. 42, No. 12, pp. 5636-5643.

(Continued)

*Primary Examiner* — Stephanie K Mummert
(74) *Attorney, Agent, or Firm* — Bond, Schoeneck & King, PLLC; Frederick Price; William Greener

(57) ABSTRACT

Methods and systems for detecting a target nucleic acid using the quantitative capabilities of real-time nucleic acid amplification systems and the multiplexing capabilities of hybridization systems, comprising: identifying a conservative sequence and a distinctive sequence within each target nucleic acid sequence; simultaneously amplifying the conservative region and the distinctive region; monitoring the amplification of the conservative region in real-time; identifying the distinctive region amplicon via multiplexed identification; and performing quantitative multiplexing analysis of the target by combining the real-time monitoring information with the multiplexed identification of the target nucleic acid.

13 Claims, 7 Drawing Sheets

Specification includes a Sequence Listing.

(56) References Cited

OTHER PUBLICATIONS

Japanese Office Action for Japanese Patent Application No. 2013-534027, dated May 12, 2015, pp. 1-6.
Innings, et al., Multiplex Real-Time PCR Targeting the RNase P RNA Gene for Detection and Identification of *Candida* Species in Blood, Journal of Clinical Microbiology, 2007, 45(3), pp. 874-880.
Hamels et al., Consensus PCR and Microarray for Diagnosis of the Genus *Staphylococcus*, Species, and Methicilin Resistance, BioTechniques, Dec. 2001, 31(6), pp. 1364-1372.
Mahony et al., Development of a Respiratory Virus Panel Test for Detection of Twenty Human Respiratory Viruses by Use of Multiplex PCR and a Fluid Microbead-Based Assay, Journal of Clinical Microbiology, 2007, 45(9), pp. 2965-2970.
Kantola et al., Real-Time Quantitative PCR Detection of Four Human Bocaviruses, Journal of Clinical Microbiology, Nov. 2010, vol. 48, No. 11, pp. 4044-4050.
Sanchez et al., Multiplex, Quantitative, Real-Time PCR Assay for Cytomegalovirus and Human DNA, Journal of Clinical Microbiology, Jul. 2002, vol. 40, No. 7, pp. 2381-2386.

\* cited by examiner

| Spotting Control | Spotting Control | Spotting Control |
|---|---|---|
| SA-1 | SA-1 | EC-1 |
| SA-2 | SA-2 | GB-4 |
| EF-1 | EF-1 | EC-1 |
| PM-1 | PM-1 | GB-4 |
| KP-1 | KP-1 | |
| KP-2 | KP-2 | |
| 25S | 25S | Spotting Control |

QUANTITATIVE MULTIPLEXED IDENTIFICATION OF NUCLEIC ACID TARGETS

CROSS-REFERENCE TO RELATED APPLICATIONS

The instant application is a divisional (DIV) of U.S. application Ser. No. 13/273,522 filed Oct. 14, 2011, which claims priority to U.S. Provisional Patent Application No. 61/393,253 entitled "Quantitative Multiplexing" filed on Oct. 14, 2010, the entire contents of which are incorporated herein by reference.

BACKGROUND OF THE INVENTION

1. Field of the Invention

The present invention relates to molecular detection, and, more specifically, to methods and systems for quantitative multiplexed detection of one or more target molecules.

2. Background of the Invention

Biochemical assays are generally used in research, clinical, environmental, and industrial settings to detect or quantify the presence or amount of certain gene sequences, antigens, diseases, or pathogens. The assays are often used to identify organisms such as parasites, fungi, bacteria, or viruses present in a host organism or sample. Under certain conditions assays may provide a measure of quantification which may be used to calculate the extent of infection or disease and to monitor the state of a disease over time. In general, biochemical assays typically detect antigens (immunoassays) or nucleic acids (nucleic acid-based or molecular assays) extracted from samples derived from research, clinical, environmental or industrial sources.

There is an increasing demand for assays for the quantitative identification of multiple pathogens across a broad range of disciplines, including homeland security, food safety, and medical diagnostics. While there is existing technology for multiplex quantitative assays, these technologies are unable to provide adequate quantitative identification of multiple pathogens. For example, microarrays provide satisfactory levels of multiplexing for the identification of DNA but provide little or no quantitative information. On the other hand, real-time PCR provides high-quality quantitative information but the level of multiplexing is limited.

Real-time polymerase chain reaction ("PCR"), also known as quantitative real time polymerase chain reaction ("qrt-PCR") among other designations, is a molecular biology tool used to simultaneously amplify a target DNA molecule using the well-known PCR process while quantifying the target DNA either as an absolute amount or a relative amount compared to another input. With standard PCR, the product is detected following completion of the reaction. To perform qrt-PCR, in contrast, the user amplifies the target DNA molecule much the same way, but detects the targeted DNA molecule in real time as the polymerase chain reaction progresses. Some of the most common methods used to detect the qrt-PCR product in real time are to utilize a non-specific fluorescent dye that incorporates into a double-stranded DNA product, or to use a sequence specific probe labeled with a fluorescent reporter that will only fluoresce when the probe hybridizes with the target sequence. If these methods are employed, for example, additional equipment such as a fluorescence detector will be required.

Sequence-specific probe methods require the use of a probe having a nucleotide base sequence that is substantially complementary to the targeted sequence or, alternatively, its amplicon. Under selective assay conditions, the probe will hybridize to the targeted sequence or its amplicon in a manner permitting a practitioner to detect the presence of the targeted sequence in a sample. Effective probes are designed to prevent nonspecific hybridization with any nucleic acid sequence that will interfere with detecting the presence of the targeted sequence. Probes and/or the amplicons may include a label capable of detection, where the label is, for example, a radiolabel, fluorescent dye, biotin, enzyme, electrochemical or chemiluminescent compound.

To quantify the qrt-PCR product, the detected fluorescence is plotted on a logarithmic scale against the cycle number. The amount of target in the pending reaction can then be determined by comparing the experimental results to standard results obtained using known amounts of product. This is, however, just one of the ways that the qrt-PCR product can be quantified.

Quantitative real-time PCR has numerous applications, particularly in the study of molecular biology. One particular use of qrt-PCR is to obtain quantitative information about pathogens in a sample. For quantitation a real-time measurement of fluorescent intensity, or real-time measurement of another parameter indicating an increased concentration of amplicons during an amplification reaction, is necessary. To differentiate multiple targets, particular primers with specific probes must be designed for each target. Or, in a less desirable case, only the primers need be designed and a dye such as SYBR Green applied to the reaction to indicate growing concentration of amplicons. For example, if there are 10 potential targets then typically 10 different probes are needed. The current state-of-the-art for detector/probe combinations allows for multiplexing of up to approximately 4 or 5 targets simultaneously. Most real-time PCR systems, however, are equipped only with two detectors for multiplexing detection. Using such a system, 6 separate PCR reactions are necessary to differentiate 6 hepatitis C virus ("HCV") genotypes.

A DNA microarray is a tool used to detect the presence of a target nucleic acid sequence in a sample resulting from hybridization of the target nucleic acid in the sample to a complementary DNA sequence on the microarray. The microarray itself is a collection of up to thousands of DNA spots—called probes (or reporters)—attached to a surface (e.g., a surface of the microarray itself or a secondary surface such as beads). Microarrays are commonly formed on microscope slides or other relatively small surfaces that can be easily read by the microarray reader. The DNA probes can range from a very short or very long segment of DNA, and often comprise a short oligo, a gene, a segment of a gene, or a non-coding segment of DNA, among many other types of sequences.

To use the microarray, the nucleic acid of interest is obtained, purified, amplified, and labeled, typically either fluorescently or with a radiolabel. The labeled nucleic acid is then washed over the DNA spots, and if the nucleic acid of interest is actually present, it will hybridize to its complementary probe on the microarray. Unbound or non-specific bound nucleic acid is washed away, leaving only bound target behind. The labeled bound target will thus generate a signal at each DNA spot where it is bound, and a microarray reader can detect the fluorescent signal while determining the identity of the probe and target based on their known location on the microarray.

One of the advantages of DNA microarray technology is the multiplexing ability of the array. Since a single array can contain up to many thousands of different probes, a single microarray experiment can perform thousands of genetic tests simultaneously. Microarrays are commonly used to: (i) analyze gene expression; (ii) identify organisms; (iii) detect single nucleotide polymorphisms ("SNPs"); and (iv) compare genomes in closely related organisms, among many other well-known uses.

Accordingly, microarray technology is often used for the multiplexed identification of DNA. However, microarrays provide very little or inaccurate quantitative information about the identified DNA. There is therefore a continued need in the art for improved methods and systems for combining quantitation with multiplexed detection.

BRIEF SUMMARY OF THE INVENTION

It is therefore a principal object and advantage of the invention to provide a method for the quantitative detection of one or more targets.

It is another object and advantage of the invention to combine quantitation with multiplexed detection of one or more targets.

It is yet another object and advantage of the invention to combine the quantitative capabilities of real-time nucleic acid amplification systems with the multiplexing capabilities of hybridization systems.

Other objects and advantages of the invention will in part be obvious, and in part appear hereinafter.

In accordance with the foregoing objects and advantages, the present invention provides a method for detecting in a sample at least one of a plurality of target nucleic acid molecules. The method comprises the steps of: (i) identifying a first region of each of the plurality of target nucleic acid molecules, where the first region is conserved among the plurality of target nucleic acid molecules; (ii) producing a first amplification product of the first region of each target nucleic acid molecule present in the sample; (iii) detecting the production of the first amplification product in real time during the amplification; (iv) identifying a second region of each of the plurality of target nucleic acid molecules, where the second region is not conserved among the plurality of target nucleic acid molecules; (v) producing a second amplification product of the second region of each target nucleic acid molecule present in the sample; and (v) detecting the second amplification product to indicate the presence of each target nucleic acid molecule present in the sample. According to another aspect, the first amplification product is produced in the presence of a first nucleic acid probe that hybridizes to the first region, and the step of detecting the amplification product in real time during the amplification comprises detecting hybridization of the first nucleic acid probe to the first region. According to another aspect, the step of detecting the second amplification product comprises hybridizing the second amplification product to a complementary probe, where the probe can be fixed to a substrate such as a DNA microarray. The method can further comprise the steps of: (i) identifying a third region of a second plurality of target nucleic acid molecules, where the third region is conserved among the second plurality of target nucleic acid molecules; (ii) producing a third amplification product by amplification of the third region of each of the second plurality of target nucleic acid molecules present in the sample; and (iii) detecting the production of the third amplification product in real time. The first amplification product and said third amplification product can be produced in the same reaction.

According to a second aspect is the above method, further comprising the step of performing quantitative multiplexed detection of each of the plurality of target nucleic acid molecules present in the sample by analyzing both the quantified amount of target nucleic acid molecules present in the sample and the detected presence of each target nucleic acid molecule present in the sample.

According to a third aspect, the presence of one or more target nucleic acid molecules in the sample indicates the presence of a pathogen in that sample. The method can be capable to detecting, quantifying, and/or identifying at least two targets—such as pathogens, genes, SNPs, specific nucleic acid sequence, etc.—in the sample.

According to a fourth aspect, the step of identifying a first region of each of the plurality of target nucleic acid molecules comprises the steps of: (i) performing a sequence alignment of at least a segment of the nucleic acid sequence of each of the plurality of target nucleic acid molecules; (ii) identifying the first region based on the sequence alignment; (iii) designing a first primer and a second primer that will amplify the first region during the PCR amplification; and (iv) designing a probe that will hybridize to the first region during the PCR amplification of the region. The probe can be designed to have a melting temperature that is at least 6° C. higher than the melting temperature of the first primer and the melting temperature of the second primer.

According to a fifth aspect, the step of identifying the second region of each of the plurality of target nucleic acid molecules comprises the steps of: (i) performing a sequence alignment of at least a segment of the nucleic acid sequence of each of the plurality of target nucleic acid molecules; (ii) identifying the second region based on the sequence alignment; and (iii) designing a first primer and a second primer that will amplify the second region during the PCR amplification. The method can also comprise the step of designing a complementary probe that will hybridize to the second region of each of the plurality of target nucleic acid molecules.

According to a sixth aspect is provided a system for detecting at least one of a plurality of target nucleic acid molecules. The system comprises: (i) a sample comprising at least one of the plurality of target nucleic acid molecules; (ii) a first primer pair, the first primer pair capable of amplifying a first region of each of the plurality of target nucleic acid molecules to produce a first amplification product, wherein the first region is conserved among the plurality of target nucleic acid molecules; (iii) a real-time Polymerase Chain Reaction ("PCR") instrument, wherein the PCR instrument is capable of producing the first amplification product using the first primer pair and is further capable of detecting the first amplification product in real time; (iv) a second primer pair, the second primer pair capable of amplifying a second region of each of the plurality of target nucleic acid molecules to produce a second amplification product, wherein the second region is not conserved among the plurality of target nucleic acid molecules; (v) a detection device for detecting the second amplification product. According to an embodiment, the system further comprises one or more of the following: a first nucleic acid probe that hybridizes to the first region; and a second nucleic acid probe that hybridizes to the second region, where the second nucleic acid probe can be fixed to a substrate such as a microarray.

According to a seventh aspect, the system can further comprise one or more of the following: (i) a third primer pair, the third primer pair capable of amplifying a third region of each of a second plurality of target nucleic acid molecules to produce a third amplification product, wherein the third region is conserved among the second plurality of target nucleic acid molecules; and (ii) means to purify nucleic acid from the sample.

According to an eighth aspect, the system is a kit for detecting in the sample at least one of a plurality of target nucleic acid molecules.

According to a ninth aspect is provided a kit for detecting at least one of a plurality of target nucleic acid molecules, the kit comprising: (i) a first primer pair, the first primer pair capable of amplifying a first region of each of the plurality of target nucleic acid molecules to produce a first amplification product, wherein the first region is conserved among the plurality of target nucleic acid molecules; (ii) a first nucleic acid probe that hybridizes to the first region; (iii) a second primer pair, the second primer pair capable of amplifying a second region of each of the plurality of target nucleic acid molecules to produce a second amplification product, wherein the second region is not conserved among said plurality of target nucleic acid molecules; and (iv) a second nucleic acid probe that hybridizes to the second region.

According to a tenth aspect, the kit can further comprise one or more of the following: (i) a microarray; and (ii) means to purify nucleic acid from the sample.

According to an eleventh aspect, the kit further comprises a third primer pair, where the third primer pair is capable of amplifying a third region of each of a second plurality of target nucleic acid molecules to produce a third amplification product, the third region being conserved among the second plurality of target nucleic acid molecules.

BRIEF DESCRIPTION OF THE SEVERAL VIEWS OF THE DRAWING(S)

The present invention will be more fully understood and appreciated by reading the following Detailed Description in conjunction with the accompanying drawings, in which:

FIG. 1 is a high-level schematic representation of a method according to one aspect of the invention;

FIG. 2 is an alignment of a 23S ribosomal RNA ("rRNA") sequence from the following bacteria: *Klebsiella pneumoniae, Escherichia coli, Proteus mirabilis, Staphylococcus aureus,* and *Enterococcus faecalis* showing the TQR primer sequences within the arrows on the upper left side and the lower right side of the aligned sequence and the TQR probe sequences within the arrows located on the upper right side of the aligned sequence;

DETAILED DESCRIPTION OF THE INVENTION

According to one aspect of the invention is a method and system to combine the quantitative capabilities of real-time nucleic acid amplification systems with the multiplexing capabilities of hybridization systems. For example, described herein are methods and systems to quantitatively analyze target nucleic acid sequences, species, or strains in a sample that contains two or more genes, species, or strains, even if those nucleic acid sequences, species, or strains are either distantly or closely related.

The term "nucleic acid" as used herein refers to a chain of nucleotides (i.e., molecules comprising a sugar lined to an exchangeable organic base. The term "nucleic acid" can also refer to oligoribonucleotides and oligodeoxyribonucleotides, as well as polynucleosides and any other organic base containing nucleic acid, including but not limited to adenine, uracil, guanine, thymine, cytosine and inosine. The nucleic acids may be single-stranded or double-stranded, and may be obtained from natural sources or through a synthetic process.

Figure 1:
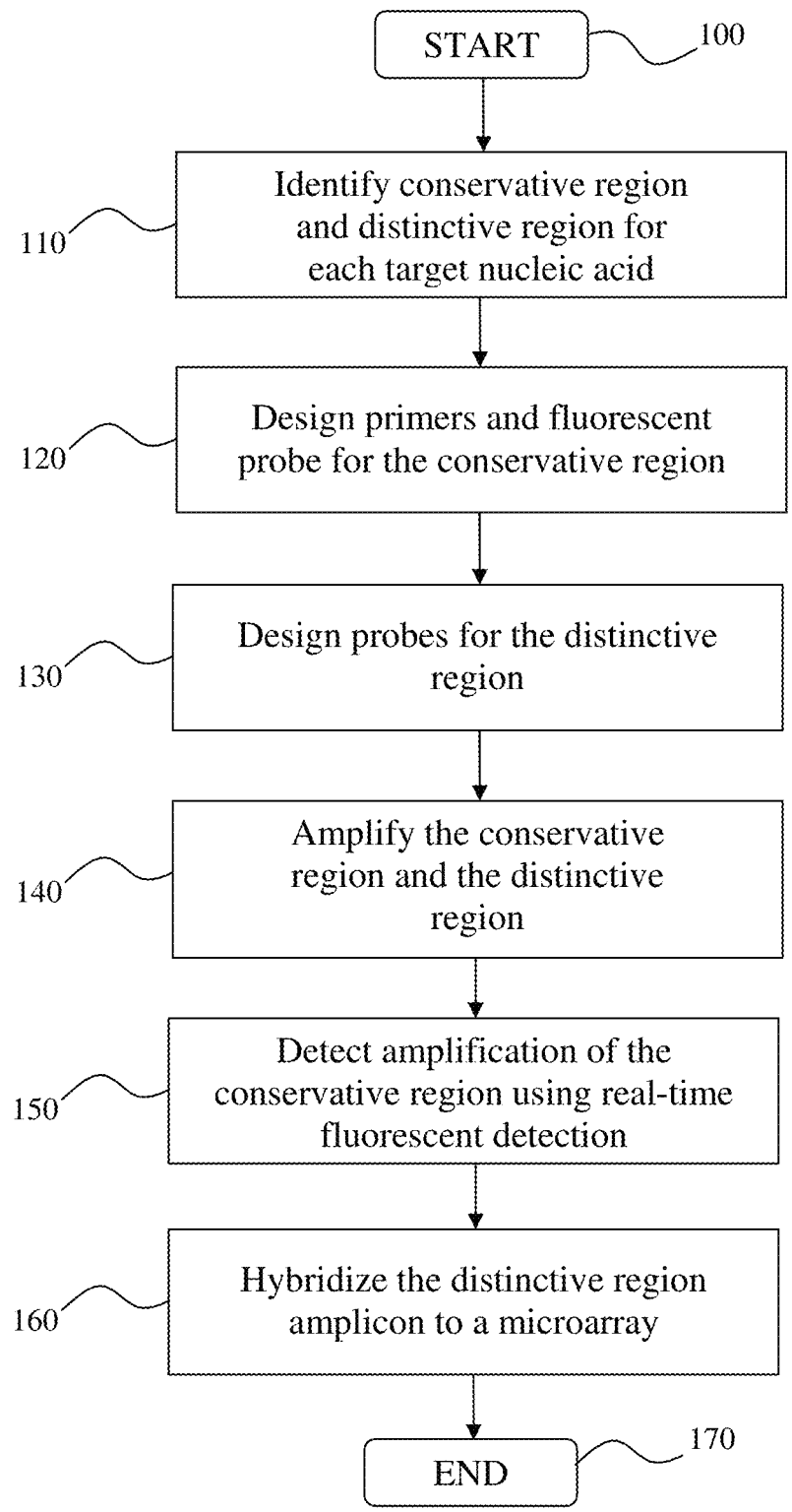

Referring now to the drawings, wherein like reference numerals refer to like parts throughout, there is seen in FIG. 1 a high-level schematic representation of a method for quantitative identification of nucleic acids in a sample according to one embodiment of the invention. As an initial step in this method, a sample is obtained for analysis. The sample can be any sample capable of being used for the described method. For example, the sample can be obtained to contain one or more nucleic acid sequences, species, or strains, among many other things. As specific examples, the sample can be any sample obtained from foodstuffs, obtained from animals or humans, or obtained from the environment, as well as any other sample obtained for, for example, identification of microbes such as pathogenic or non-pathogenic microorganisms.

Accordingly, among the many uses of the methods, devices, and systems described herein is to identify one or more microorganisms found in a potentially complex mixture of pathogenic and/or non-pathogenic microorganisms. For example, the potentially complex mixture can be a blood sample or culture obtained from a human or animal, which can contain numerous types and strains of pathogenic and/or non-pathogenic microorganisms from different of kingdoms, phylums, classes, orders, families, as well as a multitude of genera including the bacterial genera *Escherichia, Staphylococcus, Pseudomonas, Enterococcus, Klebsiella, Enterobacter, Proteus, Coxiella, Listeria, Mycobacterium, Salmonella, Bacillus,* and *Clostridium,* among many others, and viral families such as Adenoviridae, Picornaviridae, Herpesviridae, Hepadnaviridae, Flaviviridae, Retroviridae, Orthomyxoviridae, Paramyxoviridae, Papovaviridae, Polyomavirus, Rhabdoviridae, and Togaviridae, among many others. The potentially complex mixture could also be a sample obtained from any other microbial community, including from soil samples, air samples, water samples, and surface samples, among many others.

Once the sample is obtained, nucleic acid is retrieved from the sample. In one embodiment, biological material, e.g., cells or tissues, in a sample is lysed in the sample preparation process. In another embodiment, biological material is subjected to extraction. Any biological extraction protocol known in the art can be used with the method of the invention including but not limited to chemical, mechanical, electrical, sonic, thermal, etc. Any nucleic acid extraction and purification media known in the art can be used for isolating a nucleic acid of interest, including a commercial kit for nucleic acid purification manufactured or sold by providers such as QIAGEN®, Invitrogen®, and Promega®, among others.

In addition to being a sequence-specific or organism-specific retrieval of nucleic acid from the sample, the process can alternatively be designed to obtain all or almost all nucleic acid from the sample. The later will be especially advantageous, for example, in a situation where the identity of potential organisms in the sample is unknown. According to one embodiment, the nucleic acid is obtained using a method that results in nucleic acid that is suitable for immediate use in the next step of the process described herein.

The Target Quantitation Region

At step 110 of this embodiment, a first unique region is located for each target. This first region is a conservative region among the targets, and can be termed, for example, the target quantitation region ("TQR"). In one embodiment, the TQR is determined for a known set of related microorganisms, such as various bacterial families. In another embodiment, the TQR is determined for a known set of more closely-related microorganisms, such as a set of *Escherichia coli* strains comprising both pathogenic and non-pathogenic strains.

Figure 2:
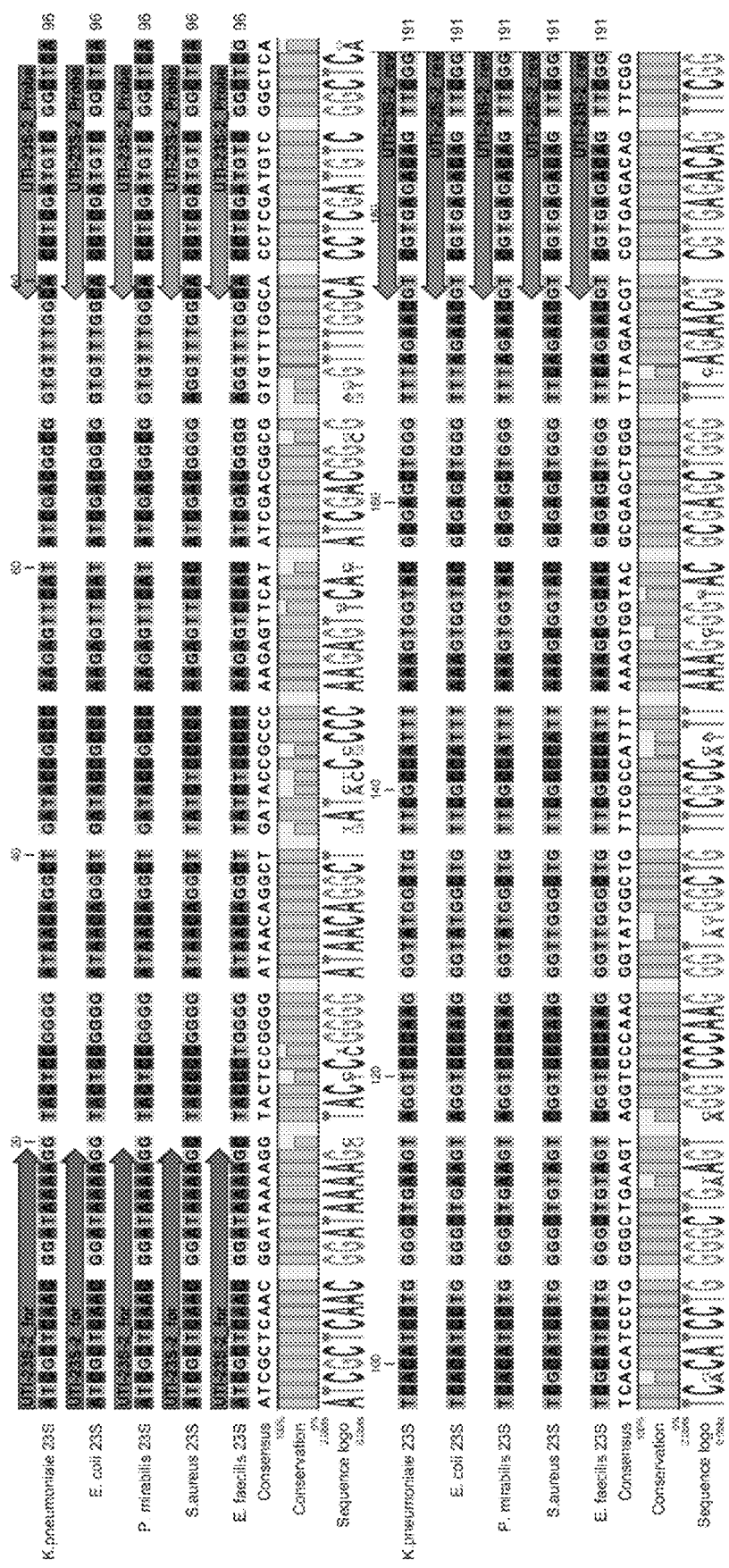

Shown in FIG. 2 is a sequence alignment of a portion of the genome from five different bacteria used to identify a TQR among the targets: *Klebsiella pneumoniae, Escherichia coli, Proteus mirabilis, Staphylococcus aureus*, and *Enterococcus faecalis*. The alignment shown in FIG. 2 aligns a DNA sequence from each organism that encodes 23S ribosomal RNA ("rRNA"). While many microorganisms contain more than one copy of the 23S rRNA gene sequence, these intra-organism sequences tend to be very highly conserved. For example, *K. pneumoniae* has 8 copies of 23S rRNA, *E. coli* has 7 copies, *P. mirabilis* has 7 copies, *S. aureus* has 5 copies, and *E. faecalis* has 4 copies. 23S rRNA is a component of the large prokaryotic 50S subunit, and typically carries the ribosomal peptidyl transferase activity of this particular rRNA. As a result of this and perhaps other functional constraints on the structure of the 23S rRNA gene sequence, the sequence contains certain regions that are highly conserved among organisms. As the sequence alignment in FIG. 2 demonstrates, this region of the 23S rRNA is highly conserved among the five bacteria.

At step 120 in the method shown in FIG. 1, primers and a fluorescent probe are designed for the TQR. Since the five bacteria shown in FIG. 2 possess a highly conserved region, this TQR can be amplified during the qrt-PCR step using a single set of forward and reverse primers for all five bacteria (as shown in FIG. 2, see forward primer "UTI-23S-2 for" and reverse primer "UTI-23S-2 rev"). Accordingly, the same primers will amplify this region from DNA obtained from all five of the bacteria depicted. In an alternative embodiment, the TQR of each target can be amplified with a distinctive set of primers, or the multiple targets can be amplified in one or more groups. It should also be noted that in addition to PCR amplification, other methods and techniques for amplification known in the art may be used to amplify and/or analyze this or any other nucleic acid sequences amplified per the methods described herein. This could include, but is not limited to, nucleic acid sequence based amplification ("NASBA"), among other methods.

The specific design of the qrt-PCR primers is an aspect of the invention. As shown in FIG. 2, the TQR region is amplified from the five bacteria using the forward primer "UTI-23S-2 for" (ATCGCTCAACGGATAAAAG) and reverse primer "UTI-23S-2 rev" (CCGAACTGTCTCAC-GAC). The qrt-PCR probe, however, comprises the sequence AGCCGACATCGAGGTG and is designed to anneal at the location "UTI-23S-2 Probe" depicted in FIG. 2. To facilitate amplification of the TQR and binding of the probe, the melting temperature, or "Tm," of the probe is preferentially 6-8° C. higher than the Tm of the forward and reverse primers. Accordingly, the primers, probe, and amplicon will have the characteristics described in TABLE 1, although other profiles are possible.

TABLE 1

Characteristics of the Primers, Probe, and Amplicon

|  | Primers | | Probe | | Amplicon | |
| --- | --- | --- | --- | --- | --- | --- |
|  | Range | Ideal | Range | Ideal | Range | Ideal |
| Length | 18-30 | 22 | 20-28 | 24 | 70-150 | 100 |
| Tm | 60-64° C. | 62° C. | 66-70° C. | 68° C. |  |  |
| GC Content | 35-65% | 50% | 35-65% | 50% |  |  |

In the example depicted in FIG. 2, for example, the primers "UTI-23S-2 for" and "UTI-23S-2 rev" and the probe "UTI-23S-2 Probe" possess the characteristics described in TABLE 2.

TABLE 2

Primers and Probe

| Primer | Sequence | Calculated Tm |
| --- | --- | --- |
| Forward primer | ATCGCTCAACGGATAAAA | 55.1 |
| Probe | AGCCGACATCGAGGTG | 62.25 |
| Reverse Primer | CCGAACTGTCTCACGAC | 56.18 |

An embodiment of a method for determining the TQR is now described. In this example, a TQR for human papilloma virus ("HPV") is being determined. As an initial step a tree of alignment is generated for two or more varieties of HPV. The alignment can be a subset of the genomes of the targets, or can be the entire genomes of the targets. Once aligned, the user or a computer program searches for the most similar sequences.

One or more sets of suitably similar sequences can then be searched by the user or a computer program to identify a region for the qrt-PCR probe. In one embodiment, it is desirable to identify potential TQRs which are: (i) identical among the aligned sequences; and (ii) 15 nucleotides or greater in length. One or more characteristics of the one or more identified potential probe regions are then analyzed by the user or a computer program. This can include the Tm, the GC score, and/or the secondary structure score for each potential probe region. For example, TABLE 3 represents a selection of potential probe regions identified in an alignment, together with the calculated Tm, GC content, and the secondary structure score for each potential region. In this example, Sequence #1 has the highest Tm (64.5° C.), and therefore might serve as the most suitable probe for the reasons discussed previously.

TABLE 3

Potential Probe Sequences

| | Sequence | Tm | GC Content | Secondary Structure Score |
|---|---|---|---|---|
| 1 | TTTGTGTGTCCGTGGTGTGCA | 64.5 | 52.4 | 13 |
| 2 | CCACCAGGTGGTGCC | 59.0 | 73.3 | 17 |
| 3 | TGACTCTATGTGCAGTACCA | 57.1 | 45.0 | 21 |
| 4 | GTAATAAAACTGCTTTTAGGCA | 54.1 | 31.8 | 21 |

As a next step in the method of determining the TQR, the region around the potential probes is analyzed. In one embodiment of the method, the following steps are performed: (i) choose the potential probe sequence with the most desirable characteristics (e.g., sequence #1); (ii) analyze approximately 200 bp flanking each side of the identified sequence to identify "standard PCR" pairs for the aligned sequences (i.e., attempt to identify a conserved region both upstream and downstream of the identified probe sequence which is conserved in all of the targets—these conserved regions can potentially serve as the binding sites for the upstream and downstream primers); and (iii) identify flanking regions that result in primers that are consistent with the probe (i.e., the Tm of the primers is approximately 6 degrees less than the Tm of the probe).

Figure 4:
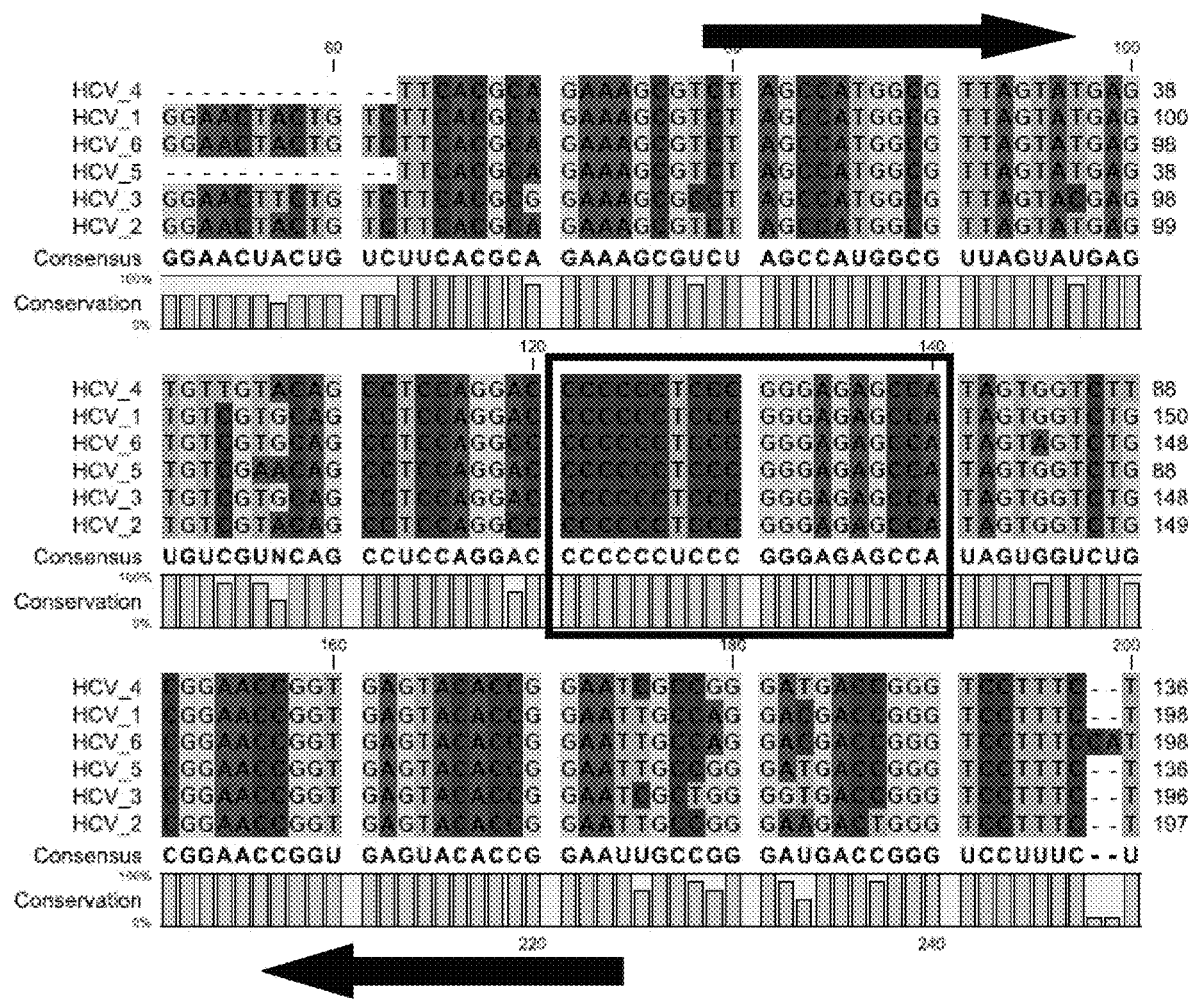
FIG. 4 is an alignment of genomic sequences from six variants of Hepatitis C virus ("HCV"), with arrows identifying the upstream and downstream primers and the potential qrt-PCR probe region boxed.

An example of one embodiment of the method for designing primers for the TQR is shown in FIG. 4. In this example, primers for a TQR for Hepatitis C virus ("HCV") have been designed. Six variants of HCV are aligned in FIG. 4 with the bases color-coded. The boxed region in the figure was selected as possessing characteristics suitable for a potential qrt-PCR probe region, and the regions flanking the potential probe region was analyzed to identify binding sites for upstream and downstream primers (identified by the arrows).

The Target Differentiation Region

Figure 3:
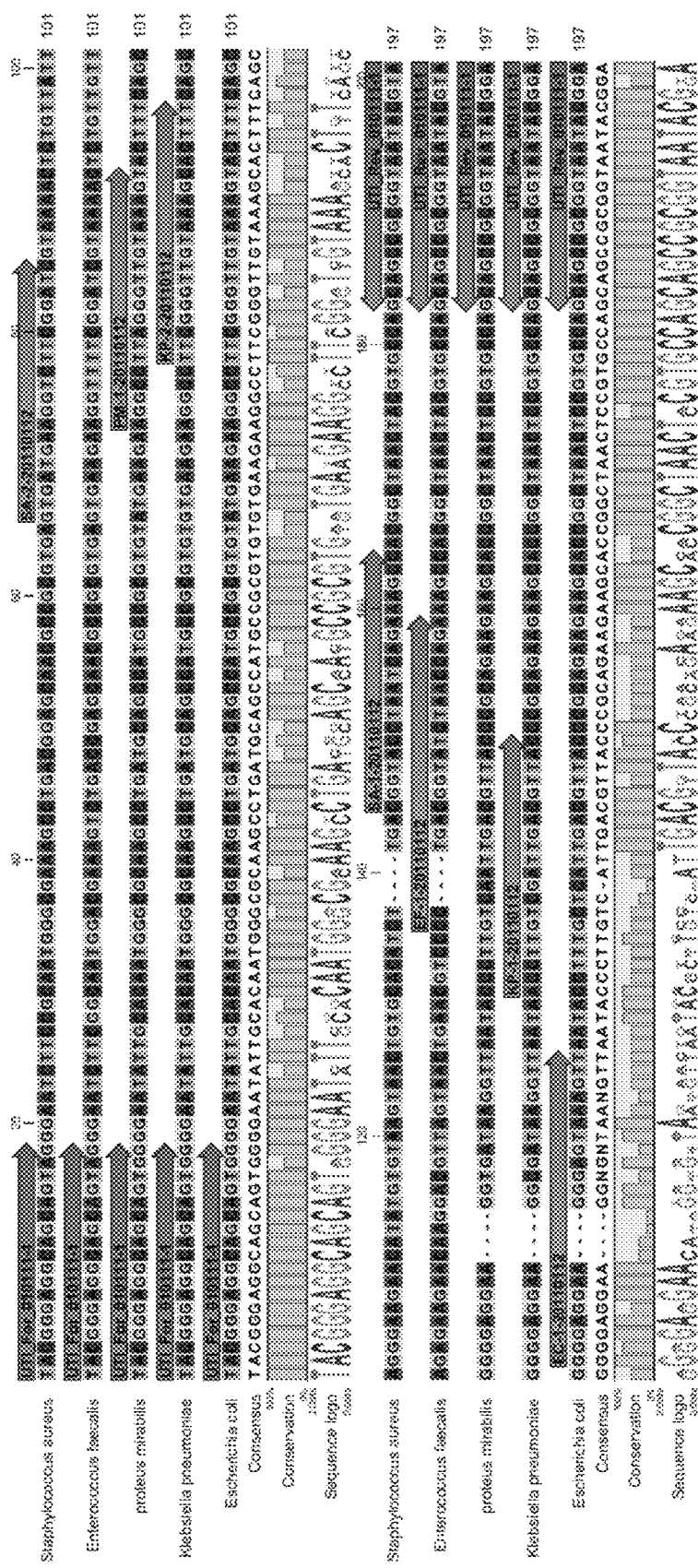
FIG. 3 is an alignment of a 16S rRNA sequence from the same five bacteria showing the TDR primer sequences within the arrows on the upper left side and the lower right side of the aligned sequences and the TDR probes within the arrows distributed through the aligned sequences in unique locations of variability between the aligned sequences.

Also at step 110 of this embodiment of the method depicted in FIG. 1, a second unique region is located in each target. In contrast with the TQR described above, the second region is a region that is distinctive among the targets, and can be termed, for example, the target differentiation region ("TDR"). The sequence alignment shown in FIG. 3 depicts a portion of the genome from the same bacteria (*Klebsiella pneumoniae*, *Escherichia coli*, *Proteus Staphylococcus aureus*, and *Enterococcus faecalis*) used to identify a TDR (the region that is a distinctive region among the targets). The alignment aligns a DNA sequence from each organism that encodes 16S rRNA. 16S rRNA is a component of the 30S subunit of prokaryotic ribosomes, and has several functions in the cell, including acting as a scaffold and aiding in the binding of the 50S and 30S subunits of prokaryotic ribosomes, among others.

At step 130 in the method shown in FIG. 1, microarray probes are designed for detection of the TDR using the microarray. As the sequence alignment in FIG. 3 demonstrates, this region of the 16S rRNA contains sub-regions that are highly conserved as well as sub-regions that are not as highly conserved. One benefit of an alignment such as this one is that the same forward ("UTI_For_010111-1") and reverse ("UTI_Rev_010111-1") primers can be employed to amplify the entire TDR, which will contain important sequence differences. In other words, the probes on the microarray can be designed such that they will be able to differentiate between the bacteria by being complementary to only one of the targets (or more than one target, depending on the needs of the user—for example, the user could design the system to recognize a subset of related targets without differentiating between the individuals in that subset by designing probes that will be complementary to a region found only in that subset, and so forth). In the example shown in FIG. 3, the probes found on the microarray—depicted by KP-1-20110112 and KP-2-20110112 for *K. pneumoniae*, EC-1-20110112 for *E. coli*, PM-1-20110112 for *P. mirabilis*, SA-1-20110112 and SA-2-20110112 for *S. aureus*, and EF-1-20110112 for *E. faecalis*—were designed to bind only the target bacteria, and only at the region shown.

Figure 5:
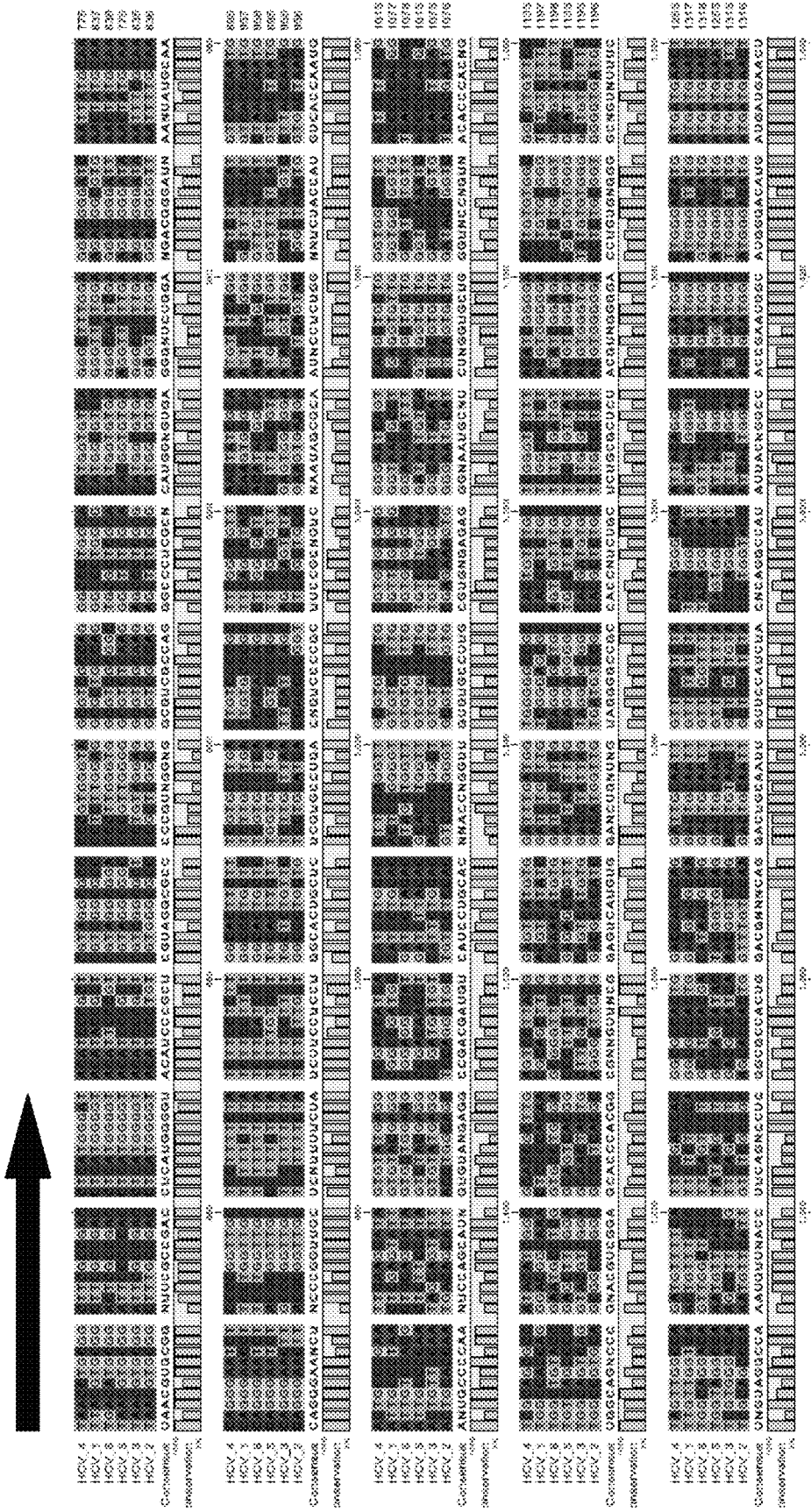
FIG. 5 is an alignment of genomic sequences from six variants of Hepatitis C virus ("HCV"), with arrows identifying the upstream and downstream primers and the potential microarray probe locations boxed.

An example of one embodiment of the method for designing primers for the TDR is shown in FIG. 5. In this example, primers and potential probes for a TDR for Hepatitis C virus ("HCV") are examined. Six variants of HCV are aligned in FIG. 5 with the bases color-coded. The upstream and downstream primers are represented by arrows, and three potential probe regions are boxed.

qrt-PCR Amplification

At step 140 in the method shown in FIG. 1, both the TQR and the TDR are amplified. The qrt-PCR reaction can be performed using any method of PCR amplification resulting in—or predicted to result in—suitable amplicons. According to one embodiment the PCR reaction is optimized using any of a variety of known methods to optimize a PCR reaction, prior to performing the qrt-PCR reaction, including but not limited varying the concentration of one or more primers, varying the annealing or extension temperature, and/or varying the extension time, among other variations.

Per one embodiment of the method, a single PCR reactor and/or reaction is used to amplify both the TQR and the TDR of multiple targets (sequences, genes, genera, species, strains, etc.). Per this method, the upstream and downstream primers for the TQR of each target are identical (see, e.g., FIG. 2), necessitating the use of a single set of primers to amplify the TQR of all targets. Similarly, the upstream and downstream primers for the TDR of each target are identical (see, e.g., FIG. 3), necessitating the use of a single set of primers to amplify the TDR of all targets. According to this embodiment, the PCR reactions can be performed either simultaneously or sequentially.

According to another embodiment, separate PCR reactions are used to amplify the TQR region and the TDR region. The TQR reaction will be a qrt-PCR reaction used for the quantitation step, and the TDR reaction will be used for the downstream application such as microarray analysis, among many others. According to this embodiment, the separate PCR reactions can occur in or on the same thermocycling device, or can occur in entirely different devices.

At step 150 in the method shown in FIG. 1, the TQR amplicon is detected during the qrt-PCR reaction. There are several possible methods which can be used to quantify the qrt-PCR products. For example, a non-specific fluorescent dye that incorporates into a double-stranded DNA product can be utilized, or a sequence-specific probe labeled with a fluorescent reporter that will only fluoresce when the probe hybridizes with the target sequence can be utilized. A fluorescence detector will likely be required if these methods are employed. Once the fluorescence data is gathered, the qrt-PCR products can be quantified using standard methods. Following step 150 of the method, quantitative information about the sample is determined using methods known in the art.

Figure 6:
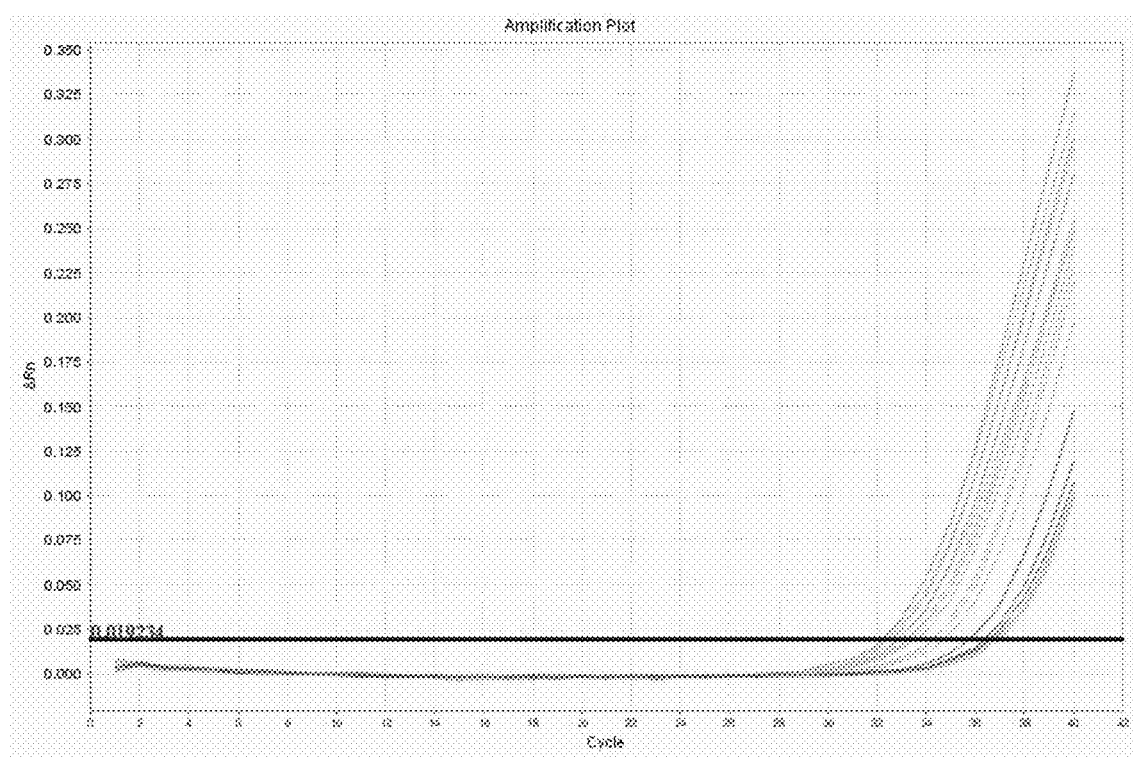
FIG. 6 is an amplification plot of the results of a qrt-PCR reaction according to one aspect of the invention.

For example, FIG. 6 is an example of an amplification plot of the results of a qrt-PCR reaction using DNA from *Klebsiella pneumoniae, Escherichia coli, Proteus Staphylococcus aureus*, and *Enterococcus faecalis* and the primers and probes depicted in FIG. 1, with the thermocycler cycle number on the x-axis and the deltaRn number—the normalized reporter ("Rn") value of an experimental reaction minus the Rn value of the baseline signal.

Microarray Detection

At step 160 in the method shown in FIG. 1, the amplicons from the TDR are exposed to a DNA microarray using any number of techniques or methods known in the art. For example, the amplicons from the TDR reaction can be washed over the DNA spots such that the TDR amplicons hybridize to the complementary probes affixed to the microarray. Unbound or non-specific bound nucleic acid is preferably washed away, leaving only bound target behind.

The microarray used in step 160 will generally comprise a solid substrate on which one or more TDR probes are immobilized. The TDR probes are immobilized on an untreated or treated surface of a substrate, preferably through covalent bonding, for specific detection of a complementary interaction with the TDR sequence amplicon from the TDR reaction. The TDR amplicon is applied through a target solution introduced onto the surface of the substrate. The probe area may be in a chamber that is hermetically sealed or open on any of the sides. The substrate can be thermoconductive and coupled to or exposed to a temperature control or heating source that provides a controllable temperature and/or environment for the hybridization and enzymatic reactions.

The bound target generates a signal at each DNA spot where it is bound, and a signal detector can detect the signal while determining the identity of the probe and target based on their known location on the microarray. A scanner detects the presence of hybridized probe sequences using an appropriate receiver for the detection elements. For example, if the detection elements are fluorescent molecules, the scanner is a fluorescence scanner for detection of the fluorescent hybridization signals. The output of the scanner is provided to a processor for analysis of the detection signals, and the processor can analyze and assess the detected target nucleotide sequences. Assessing refers to the quantitative and/or qualitative determination of the hybrid formed between the probe and nucleotide sequence. This can be an absolute value for the amount or concentration of the hybrid, or an index or ratio of a value indicative of the level of the hybrid.

A memory device or devices may be associated with the TDR microarray system, and may be embodied in a variety of different types of memory devices adapted to store digital information, such as static random access memory, dynamic random access memory, synchronous dynamic random access memory, and/or double data rate SDRAM or DRAM, as well as standard non-volatile memory such as read-only memory. The memory device may be embodied in peripheral memory storage system variations through a memory interface that allows the transfer of data to other storage devices such as hard disk drives, floppy disk drives, flash drives, optical disk drives, etc., and appropriate interfaces.

The TDR microarray detection system can be used to assay a large number of nucleic acids simultaneously. The system can be used in conjunction with a gene chip or biochip system comprising an array of oligonucleotides or nucleic acids immobilized on the substrate surface. Such a microarray can be used for any suitable purpose, such as screening an RNA sample, single nucleotide polymorphism, detection, mutation analysis, disease or infection prognosis, genome comparison, and other like applications.

Figures 7A, 7B:
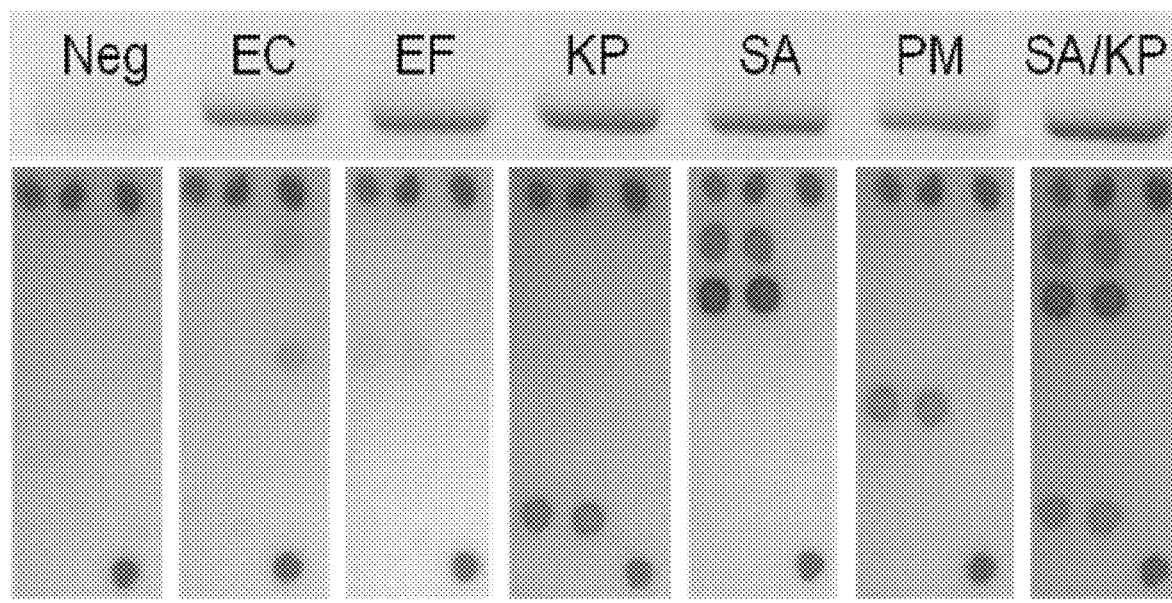
FIG. 7A is a table representing the organization of a microarray according to one aspect of the invention.
FIG. 7B shows the results of microarray analysis using a microarray as organized in FIG. 7A, where the dots represent hybridization.

For example, FIG. 7A is a table representing the organization of a microarray where "SA" is *Staphylococcus aureus*, "EC" is *Escherichia coli*, "EF" is *Enterococcus faecalis*, "PM" is *Proteus mirabilis*, and "KP" is *Klebsiella pneumoniae*. Each designation represents a TDR probe, such as the TDR probes identified in FIG. 3. FIG. 7B is an example of a microarray analysis using a microarray as organized in FIG. 7A, where the dots represent hybridization between an amplicon from the previous steps and a probe listed in FIG. 7A. For example, lane 1 ("Neg") is a control lane, and none of the bacterial probes show hybridization. Lane 3 ("KP"), in contrast, has several additional spots representing hybridization between the KP (*Klebsiella pneumoniae*) TDR product and the two DNA dots comprising the KP-2 (*Klebsiella pneumoniae*) probes. Similarly, lane 5 ("SA") shows several spots representing hybridization between the SA (*Staphylococcus aureus*) TDR product and the four DNA dots comprising the SA (*Staphylococcus aureus*) probes (i.e., SA-1 and SA-2). And lane 7 ("SA/KP"), comprising both *Klebsiella pneumonia* and *Staphylococcus aureus* TDR product, shows hybridization events for both the SA and KP probes. As lane 7 depicts, the microarray system according to the methods described herein presents a multiplexed detection system capable of distinguishing between two or more different bacterial strains. Together with the qrt-PCR steps, the system presents a highly quantitative multiplexed detection system.

It should be noted that while multiplexed detection of the quantified amplicons is described above in terms of a DNA microarray, one having skill in the art would recognize that other methods of multiplexed detection are possible, including but not limited to mass spectrometry, serial analysis of gene expression ("SAGE"), high-throughput sequencing, as well as many other hybridization methods, among other techniques. Any method, technique, system, or means capable of multiplexed differentiation of two or more DNA sequences, genes, organisms, pathogens, strains, or species can be used for the detection of the qrt-PCR amplicons.

Materials & Methods

EXAMPLE 1

Real Time PCR

DNA from *Escherichia coli* ("*E. coli*") and *Enterococcus faecalis* ("*E. faecalis*") were prepared in the laboratory of Rheonix, Inc. Other DNAs such as *Klebsiella pneumoniae* (ATCC BAA-1706D-5), *Staphylococcus aureus* (ATCC BAA-1718D-5) and *Proteus mirabilis* (ATCC 12453D) were obtained from the nonprofit biological resource center ATCC.

The concentration of each DNA was estimated by spectrophotometer (NanoDrop® 2000). All DNA samples were diluted to 10K copies per μl. This solution served as a stock to further dilute the DNA to working concentration. The total nucleic acid was isolated from a human cell line (C33A) cultured in the laboratory of Rheonix, Inc. and estimated. Thirty two nano-grams (32 ng) of the purified nucleic acid were used as background in a PCR reaction mix to mimic the nucleic acid equivalent of 10,000 genomes of human sample.

The custom designed probe and primers mix (Prime Time Assay) for 23S ribosomal gene (see FIG. 2) were obtained from Integrated DNA Technologies ("IDT"). The Prime Time Assay mix was re-suspended in IDTE buffer (10 mMTris, 0.1 mM EDTA pH8.0) as recommended by IDT. Briefly, the IDT Prime Time lyophilized assay was resuspended into 200 µl of IDTE (containing 1× Reference Dye) to obtain 10× (5 µM primers and 2.5 µM probes) concentration of probe and primer mix. The solution was stored in amber vials at −20° C. in small aliquots.

The TaqMan-Universal PCR master mix (PN #4304437) was purchased from Applied Biosystems®. StepOnePlus® Real Time PCR system from Applied Biosystems was used to carry out all quantitative PCR tests. MicroAmp® Fast Optical 96-well Reaction plates (PN #4346906) were used in the PCR reactions. The PCR reaction plates were sealed prior to carrying out the run using MicroAmp® Optical Adhesive Film (PN #4360954) from Applied Biosystems.

The Real Time PCR reaction was set up under sterile conditions to avoid any potential contamination from the environment. The reagents were opened in the laminar flow hood and set up PCR reaction prior to bringing in the microbial DNA.

The PCR reaction was set up as follows: The numbers of samples were counted. Each sample was set up in triplicate including negative control (no DNA). The volume of each sample was kept at 20 µl. The set up started by adding nuclease free water to an eppendorf tube followed by 2× Universal PCR master mix to a final concentration of 1×. 10× Prime Time Assay containing probe and primers mix were added to achieve 1× concentration (500 nM primers and 250 nM probes). The background DNA (C33A) was added and vortexed to mix the master reaction mix. The contents were spun down. The PCR master reaction mix was then distributed into individual tubes labeled for specific microbe. Each real time PCR sample was 20 µl, thus the triplicate comprised 60 µl of reaction mix. 57 µl of master reaction mix was distributed to each labeled tube, and then 3 µl of the known copies of target DNA was added to each tube. Since the DNAs were diluted in IDTE, 3 µl of IDTE was added to the negative control to make up the total volume.

TABLE 4

500 µl Reaction Mix

| Reagents | Final Concentration | Volume |
| --- | --- | --- |
| 2X Universal PCR master mix | 1x | 250 µl |
| 10X Prime Time Assay | 1x | 50 µl |
| 10K copies of C33A DNA | 10K | 50 µl |
| Target DNA (not added) | # of copies/µl | 25 µl |
| Nuclease Free water | | 125 µl |
| Total Volume | | 500 µl |

The samples were distributed in triplicate in MicroAmp® Fast Optical 96-well Reaction plates carefully to avoid any bubbles. The plate was then sealed with the film and brought to the StepOnePlus real time PCR machine which was already programmed for run.

Turn on the StepOnePlus instrument and computer, and login to the StepOnePlus software, selecting "Advance Set Up." This opens a window to select the experimental properties. For Real Time PCR the "TaqMan Reagents" was selected for "2 hours Standard PCR Amplification." The next step was to "Define the Target and Samples." Each sample was named individually. In the "Plate Layout" set-up, the target was assigned to the wells containing samples and the samples were assigned and labeled individually to each well. The individual samples and their position were further checked in "View Well Table" window. Then, returning to the set-up window, the passive fluorophore—which was ROX in this case—was selected. The next step was to select the "Run Method" window. The thermal cycle conditions were added after selecting the reaction volume per well which was 20 µl.

Following are the thermal cycling conditions used in the real time PCR reaction: (i) AmpErase activation 37° C. for 10 minutes (the 2× Universal PCR master mix contains AmpErase, an enzyme that degrades the contaminating amplicon if it is present in the reaction mix); (ii) pre-denaturation at 95° C. for 2 minutes; and (iii) 40 cycles of the following: (a) denaturation at 95° C. for 30 seconds; (b) annealing at 60° C. for 30 seconds; and (c) extension at 72° C. for 30 seconds.

The experiment was saved and the "Run" button was clicked. The samples in "Plate Layout" were highlighted to monitor the cycling. The "Analysis" window was then selected in order to select parameters such as Run vs Cycle, dRun vs Cycle or CT values, in log or linear range. The plot color could be selected by choosing the samples or target. At the completion of the run, the data was exported for analysis.

EXAMPLE 2

Microarray Analysis

The following materials were used in the micro array experiments: Reverse Dot blots ("RDB") with specific capture probes spotted in an array; amplicons (PCR amplification product 16S, amplified from specific target with biotinylated primers); 0.1N NaOH; pre-hybridization and hybridization buffer (3×SSPE (Sodium Chloride, Sodium Phosphate and EDTA buffer pH 7.5) and 0.1% SDS); RDB wash buffer (1×SSPE and 0.1% SDS); Horse Radish Peroxidase ("HRP"); and 3,3',5,5'-tetramethylbenzidine ("TMB").

The water bath and agitator were preheated to 52° C., and the pre-hybridization/hybridization buffer was placed in the water bath to bring it to the required temperature. In order to prepare the microarray on analysis membrane to properly hybridize with the amplicons produced from the earlier thermocycling, 250 µl of the pre-hybridization buffer was dispensed into the reservoir and placed the RDB into the reservoir for pre-hybridization for 15 minutes. 5 µl of amplicon was denatured at 95° C. along with 50 µl of pre-hybridization buffer for 5 minutes. The denatured amplicon was placed on ice while the RDB was in the pre-hybridization stage. The denatured amplicon (55 µl) was added to the reservoir containing RDB and incubated for 15 minutes at 52° C. Meanwhile an aliquot of wash buffer was placed in the water bath to bring it to 52° C. The RDB filters after hybridization were placed in a new reservoir containing wash buffer at 52° C. The first wash after hybridization was carried out at 52° C. for 10 minutes. The temperature of the agitator was maintained at 52° C. during pre-hybridization, hybridization, and the first wash. The second wash was carried out at room temperature for 10 minutes prior to adding HRP solution (1:500 diluted in wash buffer). RDB filters were incubated with HRP buffer for 15 minutes at room temperature. The filters were then washed with wash buffer at room temperature for 10 minutes repeating three times with agitation. The chromogenic reaction was carried out by adding TMB. The filters were incubated in TMB for 10 minutes at room temperature with gentle agitation. The reaction was stopped with water. Lastly, images were captured and analyzed.

System for Quantitative Multiplexed Detection and Identification

As described above, the method can be conducted using a series of physically separated or different analytical or experimental devices, including: a first device or area for preparation of the sample and/or purification of the nucleic acid; a second device for the qrt-PCR reaction; a third device for detection of the qrt-PCR signal; a fourth device or area for preparing the TDR amplicons for microarray analysis; a fifth device comprising the microarray; a sixth device for detection of the microarray signal; and one or more computing devices for capturing, processing, analyzing, visualizing, or otherwise using data obtained from one or more of the analytical or experimental devices. In another embodiment where microarray analysis is replaced by another method of multiplexed analysis, these experimental and detection devices will replace the microarray device listed above.

According to an aspect of the invention, the method is conducted in and/or on a single device capable of sample preparation, PCR, and electronic detection of hybridization. In various embodiments, the device can include: a sample preparation component capable of receiving a biological sample and preparing the sample for qrt-PCR and TDR; a qrt-PCR component capable of receiving the sample from the sample preparation component and performing qrt-PCR on a nucleic acid target from the sample in order to produce the qrt-PCR results; a TDR amplification component capable of receiving the sample from the sample preparation component and performing PCR on a nucleic acid target from the sample in order to produce a target amplicon; a microarray component capable of receiving the TDR target amplicon and detecting a hybridization event of the TDR target amplicon to a probe bound to a surface of the microarray; and a support comprising the sample preparation component, the qrt-PCR component, the TDR amplification component, and the microarray component.

According to an aspect of the invention, the method is conducted in an integrated microfluidic device known in the art, such as that disclosed in PCT Publication No. WO 2009/049268 A1 entitled "Integrated Microfluidic Device and Methods" by Peng Zhou et al., which is incorporated herein by reference. The method for detecting a nucleic acid target of interest in a sample disclosed herein can be readily adapted for use with an integrated microfluidic device, referred to as an assay unit or, commercially, as a CARD® (Chemistry and Reagent Device)), using methods known in the art, such as the methods disclosed in WO 2009/049268 A1.

"Microfluidics" generally refers to systems, devices, and methods for processing small volumes of fluids. Microfluidic systems can integrate a wide variety of operations for manipulating fluids. Such fluids may include chemical or biological samples. These systems also have many application areas, such as biological assays (for, e.g., medical diagnoses, drug discovery and drug delivery), biochemical sensors, or life science research in general as well as environmental analysis, industrial process monitoring and food safety testing. One type of microfluidic device is a microfluidic chip. Microfluidic chips may include micro-scale features (or "microfeatures"), such as channels, valves, pumps, reactors and/or reservoirs for storing fluids, for routing fluids to and from various locations on the chip, and/or for reacting reagents.

According to an aspect of the invention, the method is conducted in a self-contained, fully automated microfluidic device and system as disclosed in U.S. patent application Ser. No. 13/033,165 entitled "Self-Contained Biological Assay Apparatus, Methods, and Applications," the entire contents of which are hereby incorporated herein by reference. The device comprises a self-contained, fully automated, biological assay-performing apparatus including a housing; a dispensing platform including a controllably-movable reagent dispensing system, disposed in the housing; a reagent supply component disposed in the housing; a pneumatic manifold removably disposed in the housing in a space shared by the dispensing platform, removably coupled to a fluidic transport layer and a plurality of reservoirs, wherein the fluidic transport layer, the reservoirs, and a test sample to be introduced therein are disposed in the housing in the space separate from the dispensing platform; a pneumatic supply system removably coupled to the pneumatic manifold in the housing in a space separate from the dispensing platform; and a control system coupled to at least one of the dispensing platform and the pneumatic supply system, disposed in the housing.

The CARD dispensing platform can further include a motion control system operatively coupled to the reagent dispensing system, wherein the reagent dispensing system includes a reagent dispenser component having a distal dispensing end; and a camera connected to the reagent dispensing system having a field of view that includes at least a selected region of interest of the reservoirs. The camera can also include optics for obtaining data from the qrt-PCR reaction, preferably from the flat reactor setup, although other formulations are possible, including a conical reactor system. The optics used to obtain data from the qrt-PCR reaction can be, for example, any known to one of skill in the art.

According to another non-limiting aspect is an automated process for isolating, amplifying, and analyzing a target nucleic acid sequence using the CARD system. The process includes the steps of providing a pneumatic manifold that operates a microfluidic system having a fluidic transport layer and a fluidic channel disposed therein, and reservoirs attached thereto; introducing the fluid test sample into the fluidic channel; providing at least one reagent to the channel from at least one respective reservoir that is in fluid connection with the fluidic transport layer; combining the fluid test sample and the at least one reagent in a region of the fluidic transport layer, reservoir or amplification reactor; transporting the fluid test sample to a temperature-controlled amplification/reaction reactor that is in operative communication with the fluidic transport layer; incubating the fluid test sample in the amplification/reaction reactor under conditions sufficient to permit the target nucleic acid sequence to be amplified; transporting the fluid test sample to an analysis reservoir; and analyzing the amplified target nucleic acid sequence from the test sample, wherein the test sample is transported from a starting location in the fluidic transport layer to the analysis reservoir separately from any other samples and separately from the pneumatic manifold and the dispensing system.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening.

The recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not impose a limitation on the scope of the invention unless otherwise claimed.

No language in the specification should be construed as indicating any non-claimed element as essential to the practice of the invention.

It will be apparent to those skilled in the art that various modifications and variations can be made to the present invention without departing from the spirit and scope of the invention. There is no intention to limit the invention to the specific form or forms disclosed, but on the contrary, the intention is to cover all modifications, alternative constructions, and equivalents falling within the spirit and scope of the invention, as defined in the appended claims. Thus, it is intended that the present invention cover the modifications and variations of this invention provided they come within the scope of the appended claims and their equivalents.

What is claimed is:

1. A system for detecting in a sample at least one of a plurality of target nucleic acid molecules, the system comprising:

a sample comprising at least one of said plurality of target nucleic acid molecules, wherein each of said plurality of target nucleic acid molecules has a first amplification region that is conserved among said plurality of target nucleic acid molecules and a second amplification region that is not conserved among said plurality of target nucleic acid molecules, wherein for each one of the plurality of target nucleic acid molecules, the first amplification region and the second amplification region are in different locations of the nucleic acid molecule;

a first primer pair, said first primer pair capable of amplifying the first amplification region of each of said plurality of target nucleic acid molecules to produce a first amplification product;

a real-time nucleic acid amplification instrument, wherein said instrument is capable of producing said first amplification product using said first primer pair and is further capable of detecting said first amplification product in real time;

a second primer pair, said second primer pair mutually exclusive from the first primer pair and capable of, simultaneously with the production of the first amplification product, amplifying the second amplification region of each of said plurality of target nucleic acid molecules to produce a second amplification product, wherein the first amplification region and the second amplification region are in different locations of the nucleic acid molecule;

wherein the first and second amplification products are separate products; and a detection device for detecting said second amplification product.

2. The system of claim 1, further comprising a first nucleic acid probe that hybridizes to said first region.

3. The system of claim 1, further comprising a second nucleic acid probe that hybridizes to said second region.

4. The system of claim 3, wherein said second nucleic acid probe is fixed to a substrate.

5. The system of claim 4, wherein said substrate is a microarray.

6. The system of claim 1, further comprising:

a third primer pair, said third primer pair capable of amplifying a third region of each of a second plurality of target nucleic acid molecules to produce a third amplification product, wherein the third region is conserved among said second plurality of target nucleic acid molecules.

7. The system of claim 1, wherein detecting said second amplification product indicates the presence of a presence of a pathogen in said sample.

8. The system of claim 1, wherein the system is capable of detecting at least two pathogens in said sample.

9. The system of claim 1, wherein detecting said second amplification product indicates the presence of a specific nucleic acid sequence in said sample.

10. The system of claim 1, further comprising means to purify nucleic acid from said sample.

11. The system of claim 2, wherein said first nucleic acid probe has a melting temperature that is at least 6° C. higher than the melting temperature of either primer in said first primer pair.

12. The system of claim 2, wherein said system is a kit for detecting in said sample at least one of a plurality of target nucleic acid molecules.

13. The system of claim 1, wherein said real-time nucleic acid amplification instrument is a Polymerase Chain Reaction ("PCR") instrument.

* * * * *

SEQUENCE LISTING

```
<160> NUMBER OF SEQ ID NOS: 34

<210> SEQ ID NO 1
<211> LENGTH: 191
<212> TYPE: DNA
<213> ORGANISM: Klebsiella pneumonia

<400> SEQUENCE: 1
atcgctcaac ggataaaagg tactccgggg ataacaggct gataccgccc aagagttcat      60
atcgacggcg gtgtttggca cctcgatgtc ggctcatcac atcctggggc tgaagtaggt     120
cccaagggta tggctgttcg ccatttaaag tggtacgcga gctgggttta gaacgtcgtg     180
agacagttcg g                                                          191

<210> SEQ ID NO 2
<211> LENGTH: 191
<212> TYPE: DNA
<213> ORGANISM: Escherichia coli

<400> SEQUENCE: 2
atcgctcaac ggataaaagg tactccgggg ataacaggct gataccgccc aagagttcat      60
atcgacggcg gtgtttggca cctcgatgtc ggctcatcac atcctggggc tgaagtaggt     120
cccaagggta tggctgttcg ccatttaaag tggtacgcga gctgggttta gaacgtcgtg     180
agacagttcg g                                                          191

<210> SEQ ID NO 3
<211> LENGTH: 191
<212> TYPE: DNA
<213> ORGANISM: Proteus mirabilis

<400> SEQUENCE: 3
atcgctcaac ggataaaagg tactccgggg ataacaggct gataccgccc aagagttcat      60
atcgacggcg gtgtttggca cctcgatgtc ggctcatcac atcctggggc tgaagtaggt     120
cccaagggta tggctgttcg ccatttaaag tggtacgcga gctgggttta gaacgtcgtg     180
agacagttcg g                                                          191

<210> SEQ ID NO 4
<211> LENGTH: 191
<212> TYPE: DNA
<213> ORGANISM: Staphylococcus aureus
```

```
<400> SEQUENCE: 4
atcgctcaac ggataaaagc taccccgggg ataacaggct tatctccccc aagagttcac      60
atcgacgggg aggtttggca cctcgatgtc ggctcatcgc atcctggggc tgtagtcggt     120
cccaagggtt gggctgttcg cccattaaag cggtacgcga gctgggttca aacgtcgtg     180 agacagttcg g                                                         191

<210> SEQ ID NO 5
<211> LENGTH: 191
<212> TYPE: DNA
<213> ORGANISM: Enterococcus faecalis

<400> SEQUENCE: 5
atcgctcaac ggataaaagc taccctgggg ataacaggct tatctccccc aagagtccac      60
atcgacgggg aggtttggca cctcgatgtc ggctcgtcgc atcctggggc tgtagtcggt     120
cccaagggtt gggctgttcg cccattaaag cggcacgcga gctgggttca aacgtcgtg     180 agacagttcg g                                                         191

<210> SEQ ID NO 6
<211> LENGTH: 191
<212> TYPE: DNA
<213> ORGANISM: Artificial Sequence
<220> FEATURE:
<223> OTHER INFORMATION: Consensus Sequence for 23S ribosomal RNA
      through 23S ribosomal RNA 5

<400> SEQUENCE: 6
atcgctcaac ggataaaagg tactccgggg ataacaggct gataccgccc aagagttcat      60
atcgacggcg gtgtttggca cctcgatgtc ggctcatcac atcctggggc tgaagtaggt     120
cccaagggta tggctgttcg ccatttaaag tggtacgcga gctgggttta aacgtcgtg     180 agacagttcg g                                                         191

<210> SEQ ID NO 7
<211> LENGTH: 197
<212> TYPE: DNA
<213> ORGANISM: Staphylococcus aureus

<400> SEQUENCE: 7
tacgggaggc agcagtaggg aatcttccgc aatgggcgaa agcctgacgg agcaacgccg      60
cgtgagtgat gaaggtcttc ggatcgtaaa actctgttat tagggaagaa catatgtgta     120
agtaactgtg cacatcttga cggtacctaa tcagaaagcc acggctaact acgtgccagc     180
agccgcggta atacgta                                                   197

<210> SEQ ID NO 8
<211> LENGTH: 196
<212> TYPE: DNA
<213> ORGANISM: Enterococcus faecalis

<400> SEQUENCE: 8
tacgggaggc agcagtaggg aatcttcggc aatggacgaa agtctgaccg agcaacgccg      60
cgtgagtgaa gaaggttttc ggatcgtaaa actctgttgt tagagaagaa caagacgtta     120
gtaactgaac gtcccctgac ggtatctaac cagaaagcca cggctaacta cgtgccagca     180
gccgcggtaa tacgta                                                    196
```

<210> SEQ ID NO 9
<211> LENGTH: 197
<212> TYPE: DNA
<213> ORGANISM: Proteus mirabilis

<400> SEQUENCE: 9
tacgggaggc agcagtgggg aatattgcac aatgggcgca agcctgatgc agccatgccg    60
cgtgtatgaa gaaggcctta gggttgtaaa gtactttcag cggggaggaa ggtgataagg   120
ttaataccct tgtcaattga cgttacccgc agaagaagca ccggctaact ccgtgccagc   180
agccgcggta atacgga                                                  197

<210> SEQ ID NO 10
<211> LENGTH: 197
<212> TYPE: DNA
<213> ORGANISM: Klebsiella pneumonia

<400> SEQUENCE: 10
tacgggaggc agcagtgggg aatattgcac aatgggcgca agcctgatgc agccatgccg    60
cgtgtgtgaa gaaggccttc gggttgtaaa gcactttcag cggggaggaa ggcgataagg   120
ttaataacct tgtcgattga cgttacccgc agaagaagca ccggctaact ccgtgccagc   180
agccgcggta atacgga                                                  197

<210> SEQ ID NO 11
<211> LENGTH: 197
<212> TYPE: DNA
<213> ORGANISM: Escherichia coli

<400> SEQUENCE: 11
tacggaggca gcagtgggga atattgcaca atgggcgcaa gcctgatgca gccatgccgc    60
gtgtatgaag aaggccttcg ggttgtaaag tactttcagc ggggaggaag ggagtaaagt   120 taatacctttt gctcattgac gttacccgcg agaagaagca ccggctaact ccgtgccagc   180
agccgcggta atacgga                                                  197

<210> SEQ ID NO 12
<211> LENGTH: 196
<212> TYPE: DNA
<213> ORGANISM: Artificial Sequence
<220> FEATURE:
<223> OTHER INFORMATION: Consensus sequence for SEQ ID NO:7 through
      NO:11
<220> FEATURE:
<221> NAME/KEY: misc_feature
<222> LOCATION: (113)..(113)
<223> OTHER INFORMATION: n is a, c, g, or t
<220> FEATURE:
<221> NAME/KEY: misc_feature
<222> LOCATION: (115)..(115)
<223> OTHER INFORMATION: n is a, c, g, or t
<220> FEATURE:
<221> NAME/KEY: misc_feature
<222> LOCATION: (119)..(119)
<223> OTHER INFORMATION: n is a, c, g, or t

<400> SEQUENCE: 12
tacgggaggc agcagtgggg aatattgcac aatgggcgca agcctgatgc agccatgccg    60
cgtgtgtgaa gaaggccttc gggttgtaaa gcactttcag cggggaggaa ggngntaang   120 ttaatacccct tgtcattgac gttacccgca gaagaagcac cggctaactc cgtgccagca   180
gccgcggtaa tacgga                                                   196

<210> SEQ ID NO 13
<211> LENGTH: 136
<212> TYPE: DNA
<213> ORGANISM: Hepatitis C virus

<400> SEQUENCE: 13

```
ttcacgcaga aagcgtctag ccatggcgtt agcatgagtg ttgtacagcc tccaggaccc    60
cccctcccgg gagagccata gtggtcttcg gaaccggtga gtacaccgga atcgccggga   120
tgaccgggtc ctttct                                                   136
```

<210> SEQ ID NO 14
<211> LENGTH: 148
<212> TYPE: DNA
<213> ORGANISM: Hepatitus C virus

<400> SEQUENCE: 14

```
ggaactactg tcttcacgca gaaagcgtct agccatggcg ttagtatgag tgtcgtgcag    60
cctccaggac ccccctccc gggagagcca tagtggtctg cggaaccggt gagtacaccg   120
gaattgccag gacgaccggg tcctttct                                      148
```

<210> SEQ ID NO 15
<211> LENGTH: 150
<212> TYPE: DNA
<213> ORGANISM: Hepatitus C virus

<400> SEQUENCE: 15

```
ggaactactg tcttcacgca gaaagcgtct agccatggcg ttagtatgag tgtcgtgcag    60
cctccaggcc ccccctcccc gggagagcca tagtagtctg cggaaccggt gagtacaccg   120
gaattgccag gacgaccggg tcctttccat                                    150
```

<210> SEQ ID NO 16
<211> LENGTH: 136
<212> TYPE: DNA
<213> ORGANISM: Hepatitus C virus

<400> SEQUENCE: 16

```
ttcacgcaga aagcgtctag ccatggcgtt agcatgagtg tcgaacagcc tccaggaccc    60
cccctcccgg gagagccata gtggtctgcg gaaccggtga gtacaccgga attgccggga   120
tgaccgggtc ctttct                                                   136
```

<210> SEQ ID NO 17
<211> LENGTH: 148
<212> TYPE: DNA
<213> ORGANISM: Hepatitus C virus

<400> SEQUENCE: 17

```
ggaacttctg tcttcacgcg gaaagcgcct agccatggcg ttagtacgag tgtcgtgcag    60
cctccaggac ccccctccc gggagagcca tagtggtctg cggaaccggt gagtacaccg   120
gaatcgctgg ggtgaccggg tcctttct                                      148
```

<210> SEQ ID NO 18
<211> LENGTH: 148
<212> TYPE: DNA
<213> ORGANISM: Hepatitus C virus

<400> SEQUENCE: 18

```
ggaactactg tcttcacgca gaaagcgtct agccatggcg ttagtatgag tgtcgtacag    60
cctccaggcc ccccctccc gggagagcca tagtggtctg cggaaccggt gagtacaccg    120
gaattgccgg gaagactggg tcctttct                                      148
```

<210> SEQ ID NO 19
<211> LENGTH: 146
<212> TYPE: DNA
<213> ORGANISM: Artificial Sequence
<220> FEATURE:
<223> OTHER INFORMATION: Consensus sequence for SEQ ID NO:13-18
<220> FEATURE:
<221> NAME/KEY: misc_feature
<222> LOCATION: (56)..(56)
<223> OTHER INFORMATION: n is a, c, g, or t

<400> SEQUENCE: 19

```
ggaactctgt cttcacgcag aaagcgtcta gccatggcgt tagtatgagt gtcgtncagc    60
ctccaggacc ccccctcccg ggagagccat agtggtctgc ggaccggtga gtacaccgga   120
attgccggga tgaccgggtc ctttct                                        146
```

<210> SEQ ID NO 20
<211> LENGTH: 607
<212> TYPE: DNA
<213> ORGANISM: Hepatitus C virus

<400> SEQUENCE: 20

```
taacctgcgg cttcgccgac tcatgggat acatcccgct cgtaggcgcc cccgtgggta    60
gcgtcgccag ggccctggca catggtgtca gggctttgga ggacgggatc aattatgcaa  120
caagggaatc tccccggttg ctccttttct atcttcctct ggcacttct ttcgtgcctg   180
actgtcccg cttcggccgt taactatcgc aatgtctcag gcatctacca tgtcaccaat   240
gactgcccga attcaagcat agtgtatgag gccgaccatc acatcatgca ccttccaggt   300
tgcgtgccct ggtgagagag gggaatcagt cacgctgctg ggtggccctt actcctaccg   360
tcgcagcgcc atacatcggc gcaccgcttg agtccttacg gagtcatgtg gatttgatgg   420
tggggccgc tggggccgcc actgtctgct cgggtcttta catcgggacc tgtgtgggc    480
ttgttcctag ttggccagat gttttcattc cgaccacggc gccactgac cacccaggat    540
tgcaattgtt ccatctacac agggcacatt acaggccaca gaatggcctg ggacatgatg   600
atgaact                                                             607
```

<210> SEQ ID NO 21
<211> LENGTH: 599
<212> TYPE: DNA
<213> ORGANISM: Hepatitus C virus

<400> SEQUENCE: 21

```
ttacgtgcgg cttcgccgac tcatggggt acataccgct cgtcggcgcc cctcttggag    60
gcgctgccag ggccctggcg catggcgtcc gggttctgga agacggcgtg aactatgcaa  120
cagggaacct tcctggttgc tctttctcta tcttccttct ggccctgctc tcttgcctga   180
ctgtgcccgc ttcagcctac caagtgcgca attcctcggg gctttaccat gtcaccaatg   240
attgccctaa ctcgagtatt ctgtacgagg cggccgatgc catcctgcac actccggggt   300
gtgtcccttg gttcgcgagg gtaacgcctc gaggtgttgg gtggcggtga ccccacggt    360
ggccaccagg gacggcaaac tccccacaac gcagcttcga cgtcatatcg atctgcttgt   420
```

| | |
|---|---|
| cgggagcgcc accctctgct cggccctcta cgtgggggac ctgtgcgggt ctgtctttct | 480 |
| tgttggtcaa ctgtttacct tctctcccag gcgccactgg acgacgcaag actgcaattg | 540 |
| ttctatctat cccggccata acgggtca tcgcatggca tgggatatga tgatgaact | 599 |

<210> SEQ ID NO 22
<211> LENGTH: 598
<212> TYPE: DNA
<213> ORGANISM: Hepatitus C virus

<400> SEQUENCE: 22

| | |
|---|---|
| tgacatgcgg actcgccgac ctcatggggt acattcccgt cgtaggcgga cccttgggtg | 60 |
| gcgtcgcggc tgcgctcgca catggtgtga gggcaatcga ggacgggatt aactatgcaa | 120 |
| cagggaatct tcctggttgc ctttttctcta tcttcatcct ggcactgctc tcgtgcctca | 180 |
| ccacaccagc ctcggcgctc acatacggca actccagcgg gttgtaccat ctaaccaatg | 240 |
| attgtccacg ctccagcata gtgctggaag cggaggccat gatcctacac ctagctggtt | 300 |
| gtgtgccttg cgtgagagcc ggaaacattt cacgctgctg catcctgtt tcacccaccc | 360 |
| tggctgtacc gaatgcctcg gtgcctgcga gcgggttccg caaacatgtg gatctcctcg | 420 |
| caggcgctga gtcgtttgtc ttcgatgtat atcggagacc tctgcggtgc cgtatttttg | 480 |
| gcaggacagt tggctacctt cagtcctcgc atccacgaca taacgcagga ctgcaattgt | 540 |
| tcggttata caggccatgt taccggccac agaatggcgt gggacatgat gatgaact | 598 |

<210> SEQ ID NO 23
<211> LENGTH: 597
<212> TYPE: DNA
<213> ORGANISM: Hepatitus C virus

<400> SEQUENCE: 23

| | |
|---|---|
| taacgtgcgg attcccccac ctcatggggt acatcccgct cgtaggcggc cccgttgggg | 60 |
| gcgtctcaag ggctctcgca cacgtgtga aggttcttga agacgggata aactatgcaa | 120 |
| cagggaatct acccggttgc cctttctcta tctttgtcct tgcacttctt tggtgcctga | 180 |
| ccgtccccgc ttccgcagtt ccttaccgta atgcttctgg ggtttatcat gtcactaatg | 240 |
| attgcccaac tcttccatag tctacgaggc cgacaacctg atcttacacg cacctggttg | 300 |
| tgtgccctgt gtcctggaag ataatgtcag taggtgctgg gtccaaatca cccccacgct | 360 |
| gtcagcccg agcttcggag cagtcacggc ccttcttcgg agagccgttg actacttagc | 420 |
| aggaggggtg cctctcgtcc gcgttatacg tcggagacgc gtgtggggca ttatccttgg | 480 |
| taggccaaat gttcacctat aagcctcgcc agcatactac ggtgcaggac tgcaactgtt | 540 |
| ccatttacag tggccatatt accggccacc ggatggcatg ggacatgatg atgaaat | 597 |

<210> SEQ ID NO 24
<211> LENGTH: 597
<212> TYPE: DNA
<213> ORGANISM: Hepatitus C virus

<400> SEQUENCE: 24

| | |
|---|---|
| taacgtgcgg attcgccgac ctcatggggt acatccgctc gtcggcgctc ctgtaggagg | 60 |
| cgtcgcaaga gccctcgcgc atggcgtgag ggcccttgaa gacgggataa atttcgcaac | 120 |
| agggaacttg cccggttgct ccttttctat cttccttctt gctctgtttc ttgcttaatt | 180 |
| catccagcag ccagtctaga gtggcggaat acgtctggcc tctacgtcct taccaacgac | 240 |
| tgttccaata gcagtattgt gtatgaggcc gatgatgtca ttctgcacac acccggctgt | 300 |

| | |
|---|---|
| gtaccttgtg tccaggacgg caatacatct acgtgctgga ccccagtgac acctacagtg | 360 |
| gcagtcagcg tacgtcggag caactactgc ttcgatacgc agtcatgtgg acctattagt | 420 |
| aggcgcggcc acgatgtgtc tgcgctctac gtgggtgata tgtgtggggc tgtcttttcg | 480 |
| tgggacaagc cttcacgttc agacctcgac gccatcaaac ggtccagacc tgtaactgct | 540 |
| cgctgtaccc aggccatctt tcaggacatc gaatggcttg ggatatgatg atgaatt | 597 |

<210> SEQ ID NO 25
<211> LENGTH: 597
<212> TYPE: DNA
<213> ORGANISM: Hepatitus C virus

<400> SEQUENCE: 25

| | |
|---|---|
| taacgtgcgg ctttgccgac ctcatggggt acatccctgt cgtgggcgcc ccgctcggcg | 60 |
| gcgtcgccag agctctcgcg catggcgtga gagtcctgga ggacggggtt aattttgcaa | 120 |
| cagggaactt acccggttgc tccttttcta tcttcttgct ggccctgctg tcctgcatca | 180 |
| ccaccccggt ctccgctgcc gaagtgaaga acatcagtac cggctacatg gtgactaacg | 240 |
| actgcaccaa tgacagcatt acctggcagc tccaggctgt gtcctccacg tccccgggtg | 300 |
| cgtcccgtgc gagaaagtgg ggaatgcatc tcagtgctgg ataccggtct caccgaatgt | 360 |
| ggccgtgcag cggcccggcg ccctcacgca gggcttgcgg acgcacatcg acatggttgt | 420 |
| gatgtccgcc acgctctgtc tgccctctac gtggggacc tctgcggtgg ggtgatgtcg | 480 |
| cagcccaaat gttcattgtc tcgccgcagc accactggtt tgtccaagac tgcaattgct | 540 |
| ccatctaccc tggtaccatc actggacacc gcatggcatg ggacatgatg atgaact | 597 |

<210> SEQ ID NO 26
<211> LENGTH: 580
<212> TYPE: DNA
<213> ORGANISM: Artificial Sequence
<220> FEATURE:
<223> OTHER INFORMATION: Consensus sequence for SEQ ID NO:20-25
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature
<222> LOCATION: (66)..(66)
<223> OTHER INFORMATION: n is a, c, g, or t
<220> FEATURE:
<221> NAME/KEY: misc_feature
<222> LOCATION: (74)..(74)
<223> OTHER INFORMATION: n is a, c, g, or t
<220> FEATURE:
<221> NAME/KEY: misc_feature
<222> LOCATION: (81)..(81)
<223> OTHER INFORMATION: n is a, c, g, or t
<220> FEATURE:
<221> NAME/KEY: misc_feature
<222> LOCATION: (90)..(90)
<223> OTHER INFORMATION: n is a, c, g, or t
<220> FEATURE:
<221> NAME/KEY: misc_feature
<222> LOCATION: (93)..(93)
<223> OTHER INFORMATION: n is a, c, g, or t

```
<220> FEATURE:
<221> NAME/KEY: misc_feature
<222> LOCATION: (107)..(107)
<223> OTHER INFORMATION: n is a, c, g, or t
<220> FEATURE:
<221> NAME/KEY: misc_feature
<222> LOCATION: (110)..(110)
<223> OTHER INFORMATION: n is a, c, g, or t
<220> FEATURE:
<221> NAME/KEY: misc_feature
<222> LOCATION: (122)..(122)
<223> OTHER INFORMATION: n is a, c, g, or t
<220> FEATURE:
<221> NAME/KEY: misc_feature
<222> LOCATION: (161)..(161)
<223> OTHER INFORMATION: n is a, c, g, or t
<220> FEATURE:
<221> NAME/KEY: misc_feature
<222> LOCATION: (176)..(176)
<223> OTHER INFORMATION: n is a, c, g, or t
<220> FEATURE:
<221> NAME/KEY: misc_feature
<222> LOCATION: (180)..(180)
<223> OTHER INFORMATION: n is a, c, g, or t
<220> FEATURE:
<221> NAME/KEY: misc_feature
<222> LOCATION: (192)..(192)
<223> OTHER INFORMATION: n is a, c, g, or t
<220> FEATURE:
<221> NAME/KEY: misc_feature
<222> LOCATION: (200)..(201)
<223> OTHER INFORMATION: n is a, c, g, or t
<220> FEATURE:
<221> NAME/KEY: misc_feature
<222> LOCATION: (221)..(221)
<223> OTHER INFORMATION: n is a, c, g, or t
<220> FEATURE:
<221> NAME/KEY: misc_feature
<222> LOCATION: (230)..(230)
<223> OTHER INFORMATION: n is a, c, g, or t
<220> FEATURE:
<221> NAME/KEY: misc_feature
<222> LOCATION: (239)..(239)
<223> OTHER INFORMATION: n is a, c, g, or t
<220> FEATURE:
<221> NAME/KEY: misc_feature
<222> LOCATION: (245)..(245)
<223> OTHER INFORMATION: n is a, c, g, or t
<220> FEATURE:
<221> NAME/KEY: misc_feature
<222> LOCATION: (270)..(271)
<223> OTHER INFORMATION: n is a, c, g, or t
<220> FEATURE:
<221> NAME/KEY: misc_feature
<222> LOCATION: (275)..(275)
<223> OTHER INFORMATION: n is a, c, g, or t
<220> FEATURE:
<221> NAME/KEY: misc_feature
<222> LOCATION: (294)..(294)
<223> OTHER INFORMATION: n is a, c, g, or t
<220> FEATURE:
<221> NAME/KEY: misc_feature
<222> LOCATION: (302)..(302)
<223> OTHER INFORMATION: n is a, c, g, or t
<220> FEATURE:
<221> NAME/KEY: misc_feature
<222> LOCATION: (308)..(308)
<223> OTHER INFORMATION: n is a, c, g, or t
<220> FEATURE:
<221> NAME/KEY: misc_feature
<222> LOCATION: (312)..(312)
<223> OTHER INFORMATION: n is a, c, g, or t
<220> FEATURE:
<221> NAME/KEY: misc_feature
<222> LOCATION: (323)..(323)
<223> OTHER INFORMATION: n is a, c, g, or t
```

```
<220> FEATURE:
<221> NAME/KEY: misc_feature
<222> LOCATION: (326)..(326)
<223> OTHER INFORMATION: n is a, c, g, or t
<220> FEATURE:
<221> NAME/KEY: misc_feature
<222> LOCATION: (329)..(329)
<223> OTHER INFORMATION: n is a, c, g, or t
<220> FEATURE:
<221> NAME/KEY: misc_feature
<222> LOCATION: (339)..(339)
<223> OTHER INFORMATION: n is a, c, g, or t
<220> FEATURE:
<221> NAME/KEY: misc_feature
<222> LOCATION: (347)..(347)
<223> OTHER INFORMATION: n is a, c, g, or t
<220> FEATURE:
<221> NAME/KEY: misc_feature
<222> LOCATION: (352)..(352)
<223> OTHER INFORMATION: n is a, c, g, or t
<220> FEATURE:
<221> NAME/KEY: misc_feature
<222> LOCATION: (373)..(374)
<223> OTHER INFORMATION: n is a, c, g, or t
<220> FEATURE:
<221> NAME/KEY: misc_feature
<222> LOCATION: (378)..(378)
<223> OTHER INFORMATION: n is a, c, g, or t
<220> FEATURE:
<221> NAME/KEY: misc_feature
<222> LOCATION: (393)..(393)
<223> OTHER INFORMATION: n is a, c, g, or t
<220> FEATURE:
<221> NAME/KEY: misc_feature
<222> LOCATION: (397)..(397)
<223> OTHER INFORMATION: n is a, c, g, or t
<220> FEATURE:
<221> NAME/KEY: misc_feature
<222> LOCATION: (399)..(399)
<223> OTHER INFORMATION: n is a, c, g, or t
<220> FEATURE:
<221> NAME/KEY: misc_feature
<222> LOCATION: (415)..(415)
<223> OTHER INFORMATION: n is a, c, g, or t
<220> FEATURE:
<221> NAME/KEY: misc_feature
<222> LOCATION: (435)..(435)
<223> OTHER INFORMATION: n is a, c, g, or t
<220> FEATURE:
<221> NAME/KEY: misc_feature
<222> LOCATION: (447)..(447)
<223> OTHER INFORMATION: n is a, c, g, or t
<220> FEATURE:
<221> NAME/KEY: misc_feature
<222> LOCATION: (453)..(453)
<223> OTHER INFORMATION: n is a, c, g, or t
<220> FEATURE:
<221> NAME/KEY: misc_feature
<222> LOCATION: (456)..(456)
<223> OTHER INFORMATION: n is a, c, g, or t
<220> FEATURE:
<221> NAME/KEY: misc_feature
<222> LOCATION: (462)..(462)
<223> OTHER INFORMATION: n is a, c, g, or t
<220> FEATURE:
<221> NAME/KEY: misc_feature
<222> LOCATION: (477)..(477)
<223> OTHER INFORMATION: n is a, c, g, or t
<220> FEATURE:
<221> NAME/KEY: misc_feature
<222> LOCATION: (486)..(486)
<223> OTHER INFORMATION: n is a, c, g, or t
<220> FEATURE:
<221> NAME/KEY: misc_feature
<222> LOCATION: (505)..(507)
<223> OTHER INFORMATION: n is a, c, g, or t
```

<220> FEATURE:
<221> NAME/KEY: misc_feature
<222> LOCATION: (532)..(532)
<223> OTHER INFORMATION: n is a, c, g, or t
<220> FEATURE:
<221> NAME/KEY: misc_feature
<222> LOCATION: (546)..(546)
<223> OTHER INFORMATION: n is a, c, g, or t

<400> SEQUENCE: 26

```
ctcatggggt acatcccgct cgtaggcgcc cccgtnggng gcgtcgccag cgccctcgcn    60
catggngtga gggntctgga ngacgggatn aantatgcaa caggaanctn cccggttgct   120
cnttttctat cttcctcctg gcactgctct cgtgcctgac ngtccccgct tccgcngtcn   180
aatagcgcaa tncctctggn ntctaccatg tcaccaatga ntgccccaan tccagcatng   240
tgtangaggc cgacgatgtc atcctgcacn naccnggttg tgtgccttgc gtgngagagg   300
gnaatgcntc tnggtgctgg gtnccngtna caccccacng tggcagnccc gnacgtcgga   360
gcacccacgg cgnngttncg gagtcatgtg ganctgntng taggggccgc caccntctgc   420
tctgcgctct acgtngggga cctgtgnggg gcngtntttc tngtaggcca aatgttnacc   480
ttcagncctc ggcgccactg gacgnnncag gactgcaatt gttccatcta cncaggccat   540
attacnggcc accgaatggc atgggacatg atgatgaact                          580
```

<210> SEQ ID NO 27
<211> LENGTH: 19
<212> TYPE: DNA
<213> ORGANISM: Artificial Sequence
<220> FEATURE:
<223> OTHER INFORMATION: Primer

<400> SEQUENCE: 27

```
atcgctcaac ggataaaag                                                 19
```

<210> SEQ ID NO 28
<211> LENGTH: 17
<212> TYPE: DNA
<213> ORGANISM: Artificial sequence
<220> FEATURE:
<223> OTHER INFORMATION: Primer

<400> SEQUENCE: 28

```
ccgaactgtc tcacgac                                                   17
```

<210> SEQ ID NO 29
<211> LENGTH: 16
<212> TYPE: DNA
<213> ORGANISM: Artificial sequence
<220> FEATURE:
<223> OTHER INFORMATION: Primer

<400> SEQUENCE: 29

```
agccgacatc gaggtg                                                    16
```

<210> SEQ ID NO 30
<211> LENGTH: 18
<212> TYPE: DNA
<213> ORGANISM: Artificial sequence
<220> FEATURE:
<223> OTHER INFORMATION: Primer

<400> SEQUENCE: 30

```
atcgctcaac ggataaaa                                                  18
```

```
<210> SEQ ID NO 31
<211> LENGTH: 21
<212> TYPE: DNA
<213> ORGANISM: Artificial sequence
<220> FEATURE:
<223> OTHER INFORMATION: Primer

<400> SEQUENCE: 31
tttgtgtgtc cgtggtgtgc a                                          21

<210> SEQ ID NO 32
<211> LENGTH: 15
<212> TYPE: DNA
<213> ORGANISM: Artificial sequence
<220> FEATURE:
<223> OTHER INFORMATION: Primer

<400> SEQUENCE: 32
ccaccaggtg gtgcc                                                 15

<210> SEQ ID NO 33
<211> LENGTH: 20
<212> TYPE: DNA
<213> ORGANISM: Artificial sequence
<220> FEATURE:
<223> OTHER INFORMATION: Primer

<400> SEQUENCE: 33
tgactctatg tgcagtacca                                            20

<210> SEQ ID NO 34
<211> LENGTH: 22
<212> TYPE: DNA
<213> ORGANISM: Artificial sequence
<220> FEATURE:
<223> OTHER INFORMATION: Primer

<400> SEQUENCE: 34
gtaataaaac tgcttttagg ca                                         22
```